(12) United States Patent
Bayley et al.

(10) Patent No.: US 11,592,382 B2
(45) Date of Patent: *Feb. 28, 2023

(54) METHOD OF ANALYZING POST-TRANSLATIONAL MODIFICATIONS

(71) Applicant: OXFORD UNIVERSITY INNOVATION LIMITED, Oxford (GB)

(72) Inventors: John Hagan Pryce Bayley, Oxford (GB); David Rodriguez-Larrea, Oxford (GB); Christian Bech Rosen, Aarhus C (DK)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/884,367

(22) Filed: May 27, 2020

(65) Prior Publication Data

US 2021/0096053 A1 Apr. 1, 2021

Related U.S. Application Data

(63) Continuation of application No. 15/023,652, filed as application No. PCT/GB2014/052873 on Sep. 22, 2014, now Pat. No. 10,712,254.

(60) Provisional application No. 61/896,933, filed on Oct. 29, 2013.

(30) Foreign Application Priority Data

Sep. 23, 2013 (GB) .................................... 1316849

(51) Int. Cl.
*G01N 15/10* (2006.01)
*G01N 33/68* (2006.01)
*A61K 38/00* (2006.01)
*G01N 33/487* (2006.01)

(52) U.S. Cl.
CPC ......... *G01N 15/1031* (2013.01); *A61K 38/00* (2013.01); *G01N 33/48721* (2013.01); *G01N 33/6842* (2013.01); *G01N 2440/10* (2013.01); *G01N 2800/00* (2013.01)

(58) Field of Classification Search
CPC ............. A61K 38/00; G01N 33/48721; G01N 33/6842; G01N 2440/00; G01N 2440/10; G01N 2440/20; G01N 2440/12; G01N 2440/14; G01N 2440/24; G01N 2440/26; G01N 2440/28; G01N 2440/30; G01N 2440/32; G01N 2440/36; G01N 2440/38; G01N 2440/40; G01N 5/1031; C07K 2/00; C07K 4/00

See application file for complete search history.

(56) References Cited

U.S. PATENT DOCUMENTS

| 8,105,846 | B2 | 1/2012 | Bayley et al. |
| 8,785,211 | B2 | 7/2014 | Bayley et al. |
| 8,822,160 | B2 | 9/2014 | Bayley et al. |
| 9,562,887 | B2 | 2/2017 | Maglia et al. |
| 9,732,381 | B2 | 8/2017 | Stoddart et al. |
| 10,712,254 | B2 * | 7/2020 | Bayley ............. G01N 33/48721 |
| 2003/0207326 | A1 | 11/2003 | Su et al. |
| 2011/0311965 | A1 | 12/2011 | Maglia et al. |
| 2012/0107802 | A1 | 5/2012 | Stoddart et al. |
| 2015/0008126 | A1 | 1/2015 | Maglia et al. |

FOREIGN PATENT DOCUMENTS

| WO | 00/028312 | A1 | 5/2000 | |
| WO | 2005/052591 | A1 | 6/2005 | |
| WO | 2006/100484 | A2 | 9/2006 | |
| WO | 2008102120 | A1 | 8/2008 | |
| WO | 2008102121 | A1 | 8/2008 | |
| WO | 2009/077734 | A2 | 6/2009 | |
| WO | 2010/004265 | A1 | 1/2010 | |
| WO | 2010/004273 | A1 | 1/2010 | |
| WO | 2010/055307 | A1 | 5/2010 | |
| WO | 2010/086603 | A1 | 8/2010 | |
| WO | 2011/067559 | A1 | 6/2011 | |
| WO | 2012/164270 | A1 | 12/2012 | |
| WO | WO-2012164270 | A1 * | 12/2012 | ............. B82Y 15/00 |
| WO | 2013/116509 | A1 | 8/2013 | |
| WO | 2013/121201 | A1 | 8/2013 | |
| WO | 2013/123379 | A2 | 8/2013 | |
| WO | WO-2013123379 | A2 * | 8/2013 | ............. C12M 47/06 |
| WO | 2014/014347 | A1 | 1/2014 | |

OTHER PUBLICATIONS

Ying et al. "Recognizing the translocation signals of individual peptide-oligonucleotide conjugates using an a-hemolysin nanopore", Chem. Commun., 2012, 8784-8786 (Year: 2012).*
U.S. Appl. No. 15/023,652, filed Mar. 21, 2016, John Hagan Bayle.
U.S. Appl. No. 12/093,610, filed Jul. 28, 2008, Hagan Bayley.
U.S. Appl. No. 13/338,794, filed Dec. 28, 2011, Hagan Bayley.
U.S. Appl. No. 12/681,643, filed Jun. 15, 2010, John Hagan Bayley.
U.S. Appl. No. 13/129,278, filed Aug. 26, 2011, Giovanni Maglia.
U.S. Appl. No. 14/334,285, filed Jul. 17, 2014, Giovanni Maglia.
U.S. Appl. No. 13/260,178, filed Jan. 17, 2012, David Stoddart.
U.S. Appl. No. 15/023,652, filed Mar. 4, 2020, L. Garyu.
U.S. Appl. No. 15/023,652, filed Feb. 27, 2020, L. Garyu.
U.S. Appl. No. 15/023,652, filed Jul. 9, 2019, L. Garyu.
U.S. Appl. No. 15/023,652, filed Nov. 27, 2018, L. Garyu.
U.S. Appl. No. 15/023,652, filed Jun. 29, 2018, L. Garyu.
U.S. Appl. No. 12/093,610, filed Sep. 27, 2011, S. T. Kapushoc.

(Continued)

*Primary Examiner* — Lianko G Garyu
(74) *Attorney, Agent, or Firm* — Nelson Mullins Riley & Scarborough LLP; Jane E. Remillard, Esq.; Christopher L. Frank

(57) ABSTRACT

The invention relates to a new method of determining the presence, absence, number or position(s) of one or more post-translational modifications in a peptide, polypeptide or protein. The invention uses transmembrane pores.

19 Claims, 10 Drawing Sheets

Specification includes a Sequence Listing.

(56) References Cited

OTHER PUBLICATIONS

U.S. Appl. No. 12/093,610, filed Apr. 4, 2011, S. T. Kapushoc.
U.S. Appl. No. 12/093,610, filed Sep. 29, 2010, S. T. Kapushoc.
U.S. Appl. No. 12/093,610, filed Jan. 22, 2010, S. T. Kapushoc.
U.S. Appl. No. 12/093,610, filed Oct. 6, 2009, S. T. Kapushoc.
U.S. Appl. No. 13/338,794, filed Mar. 13, 2014, S. T. Kapushoc.
U.S. Appl. No. 13/338,794, filed Mar. 5, 2013, S. T. Kapushoc.
U.S. Appl. No. 13/338,794, filed Sep. 24, 2012, S. T. Kapushoc.
U.S. Appl. No. 13/338,794, filed Jul. 19, 2012, S. T. Kapushoc.
U.S. Appl. No. 12/681,643, filed Apr. 24, 2014, R. Li.
U.S. Appl. No. 12/681,643, filed Nov. 6, 2013, R. Li.
U.S. Appl. No. 12/681,643, filed Mar. 8, 2013, R. Li.
U.S. Appl. No. 12/681,643, filed Jul. 10, 2012, R. Li.
U.S. Appl. No. 12/681,643, filed Dec. 21, 2011, R. Li.
U.S. Appl. No. 12/681,643, filed Sep. 6, 2011, R. Li.
U.S. Appl. No. 13/129,278, filed Feb. 18, 2014, R. Li.
U.S. Appl. No. 13/129,278, filed Jun. 11, 2013, R. Li.
U.S. Appl. No. 13/129,278, filed Feb. 27, 2013, R. Li.
U.S. Appl. No. 14/334,285, filed Sep. 28, 2016, R. Li.
U.S. Appl. No. 14/334,285, filed May 11, 2016, R. Li.
U.S. Appl. No. 14/334,285, filed Dec. 3, 2015, R. Li.
U.S. Appl. No. 14/334,285, filed Aug. 21, 2015, R. Li.
U.S. Appl. No. 14/334,285, filed Feb. 9, 2015, R. Li.
U.S. Appl. No. 13/260,178, filed Apr. 7, 2017, R. Crow.
U.S. Appl. No. 13/260,178, filed Jul. 21, 2016, R. Li.
U.S. Appl. No. 13/260,178, filed Aug. 18, 2015, R. Li.
U.S. Appl. No. 13/260,178, filed Feb. 26, 2015, R. Li.
U.S. Appl. No. 13/260,178, filed Jan. 14, 2014, R. Li.
U.S. Appl. No. 13/260,178, filed May 9, 2013, R. Li.
U.S. Appl. No. 13/260,178, filed Feb. 20, 2013, R. Li.
Rosen et al., "Single-molecule site-specific detection of protein phosphorylation with a Nanopore," Nature Biotechnology, 32:179-181 (2014).
Rotem, D., et al., "Protein detection by nanopores equipped with aptamers," J. Am. Chem. Soc., 134: 2781-2787 (2012).
Shin, S.H., et al., "Formation of a chiral center and pyrimidal inversion at the single-molecule level," Angew. Chem. Int. Ed. Engl, 46: 7412-7416 (2007).
Stoddart et al., "Single-nucleotide discrimination in immobilized DNA oligonucleotides with a biological nanopore," PNAS, 106(19): 7702-7707 (2009).
Talaga, D. et al., "Single-Molecule Protein Unfolding in Solid State Nanopores," JACS, vol. 131: 9287-9297 (2009).
Unlu, M., et al., "Difference gel electrophoresis: a single gel method for detecting changes in protein extracts," Electrophoresis, 18: 2071-2077 (1997).
van Heel M. et al., "Single-particle electron cryo-microscopy: towards atomic resolution," Q Rev Biophys. 33: 307-369 (2000).
Van Lengerich, B., et al. "Covalent attachment of lipid vesicles to a fluid-supported bilayer allows observation of DNA-mediated vesicle interactions," Langmuir, 26(11): 8666-8672 (2010).
Wallace, E.V. et al. "Identification of epigenetic DNA modifications with a protein nanopore," Chem. Commun., 46: 8195-8197 (2010).
Wu, H.C. et al.,"Single-molecule detection of nitrogen mustards by covalent reaction within a protein nanopore," J. Am. Chem. Soc., 130 6813-6819 (2008).
Xie, H. et al., "Single-molecule observation of the catalytic subunit of cAMP-dependent protein kinase binding to an inhibitor peptide," Chem. Biol. 12: 109-120 (2005).
Yoshina-Ishii, C. et al., "Arrays of mobile tethered vesicles on supported lipid bilayers," J Am Chern Soc ., 125(13): 3696-3697 (2003).
Zhao et al., "Single-molecule spectroscopy of amino acids and peptides by recognition tunnelling," Nature Nanotechnology, 9: 466-473 (2014).
Niemeyer, C. "Semisynthetic DNA-Protein Conjugates for Biosensing and Nanofabrication," Angew. Chem. Int. Ed., vol. 49(7): 1200-1216 (2010).
Altschul S. F., "A protein alignment scoring system sensitive at all evolutionary distances.," J Mol Evol., 36:290-300 (1993).
Altschul, S.F et al., "Basic local alignment search tool," J Mol Biol. 215:403-410 (1990).
Bayley, H. et al. "Droplet interface bilayers," Mol. Biosyst., 4:1191-1208 (2008).
Bayley, H., "Are we there yet?: Comment on" Nanopores: A journey towards DNA sequencing by Meni Wanunu, Phys. Life Rev., 9: 161-163 (2012).
Bayley, H., "Sequencing single molecules of DNA," Curr. Opin. Chem. Biol. 10: 628-637 (2006).
Bayley, H., et al., "Stochastic sensors inspired by biology," Nature, 413 226-230 (2001).
Braha et al., "Designed protein pores as components for biosensors," Chem Biol., 4(7):497-505 (1997).
Braha, O. et al., "Simultaneous stochastic sensing of divalent metalions," Nat. Biotechnol., 18: 1005-1007 (2000).
Branton, D. et al., "The potential and challenges of nanopore sequencing," Nat. Biotechnol. 26:1146-1153 (2008).
Brooks, C.L., et al., "New insights into p53 activation," Cell Res., 20: 614-621 (2010).
Cherf, G.M. et al., "Automated forward and reverse ratcheting of DNA in a nanopore at 5-A precision," Nat. Biotechnol. 30: 344-348 (2012).
Choudhary, C. et al., "Decoding signalling networks by mass spectrometry-based proteomics," Nat. Rev. Mol. Cell. Biol., 11:427-439 (2010).
Chu, J., et al., "Real-time monitoring of DNA polymerase function and stepwise single-nucleotide DNA strand translocation through a protein nanopore," Angew. Chem. Int. Ed. Engl., 49:10106-10109 (2010).
Cockroft, S.L., et al. "A single-molecule nanopore device detects DNA polymerase activity with single-nucleotide resolution," J. Am. Chem. Soc., 130:818-820 (2008).
Cohen,P. "The role of protein phosphorylation in human health and disease. The Sir Hans Krebs Medal Lecture," European Journal of Biochemistry, 268, Issue 19: 5001-5010 (2001).
Derrington, I.M. et al., "Nanopore DNA sequencing with MspA," Proc. Natl. Acad. Sci. U.S.A. 107:16060-16065 (2010).
Devereux et al.,"A comprehensive set of sequence analysis programs for the VAX," Nucleic Acids Research 12:387-395 (1984).
Domon, B. et al., "Mass spectrometry and protein analysis," Science, 312:212-217 (2006).
Gonzalez-Perez et al., "Biomimetic triblock copolymer membrane arrays: a stable template for functional membrane proteins," Langmuir, 25: 10447-10450 (2009).
Gorg, A., et al., "Current two-dimensional electrophoresis technology for proteomics," Proteomics, 4 :3665-3685 (2004).
Hall AR et al., "Hybrid pore formation by directed insertion of ?-haemolysin into solid-state nanopores," Nat Nanotechnol., 5: 874-877 (2010).
Hayden, E.C., "Sequence set to alter clinical landscape," Nature 482: 288 (2012).
Holden et al., "Functional bionetworks from nanoliter water droplets," J Am Chem Soc., 129(27):8650-8665 (2007).
Holden, M.A. et al., "Direct introduction of single protein channels and pores into lipid bilayers," J. Am. Chem. Soc., 127: 6502-6503 (2005).
Howorka, S. et al., "Nanopore analytics: sensing of single molecules," Chem. Soc. Rev., 38: 2360-2384 (2009).
Howorka, S., et al., "Stochastic detection of monovalent and bivalent protein-ligand interactions," Angew. Chem. Int. Ed. Engl., 43: 842-846 (2004).
Huttlin, E.Lm et al.,"A tissue-specific atlas of mouse protein phosphorylation and expression," Cell, 143:1174-1189 (2010).
Kang, X.F et al., "Stochastic detection of enantiomers," J. Am. Chem. Soc., 128:10684-10685 (2006).
Khoury, G.A., et al., "Proteome-wide post-translational modification statistics: frequency analysis and curation of the swiss-prot database," Sci. Rep. 1 (2011).
Kruse, J.P. et al., "SnapShot: p53 posttranslational modifications," Cell, 133:930 (2008).

(56) References Cited

OTHER PUBLICATIONS

Larrea et al., "Multistep protein unfolding during nanopore translocation", Nature Nanotechnology, vol. 8: 288-295 (2013).
Lieberman, K.R. et al., "Processive replication of single DNA molecules in a nanopore catalyzed by phi29 DNA polymerase," J. Am. Chem. Soc., 132:17961-17972 (2010).
Maclaine, J.M. et al., "How phosphorylation controls p53," Cell Cycle, 10: 916-921 (2011).
Maglia, G., et al., "Analysis of single nucleic acid molecules with protein nanopores," Methods Enzymol., 475: 591-623 (2010).
Manrao E.A. et al., "Reading DNA at single-nucleotide resolution with a mutant MspA nanopore and phi29 DNA polymerase," Nat. Biotechnol. 30: 349-353 (2012).
Manrao, E.A., et al., "Nucleotide discrimination with DNA immobilized in the MspA nanopore," PLoS One, 6 (2011).
Merstorf, C. et al., "Wild type, mutant protein unfolding and phase transition detected by single-nanopore recording," ACS Chem. Biol., 7:652-658 (2012).
Mertins, P. et al. "Integrated proteomic analysis of post-translational modifications by serial enrichment," Nat. Methods, 10:634-637 (2013).
Montal and Mueller, "Formation of bimolecular membranes from lipid monolayers and a study of their electrical properties," Proc. Natl. Acad. Sci. USA., 69:3561-3566 (1972).
Movileanu, L., et al., "Detecting protein analytes that modulate transmembrane movement of a polymer chain within a single protein pore," Nat. Biotechnol., 18: 1091-1095 (2000).
Murphy, PJ et al., "Single-molecule analysis of combinatorial epigenomic states in normal and tumor cells," Proceedings of the National Academy of Sciences, 110(19): 7772-7777 (2013).
Narayana, N., et al., "Crystal structure of a polyhistidine-tagged recombinant catalytic subunit of cAMP-dependent protein kinase complexed with the peptide inhibitor PKI(5-24) and adenosine," Biochemistry, 36:4438-4448 (1997).
Nikolov, V., et al., "Behavior of giant vesicles with anchored DNA molecules." Biophys J 92(12): 4356-4368 (2007).
Nivala et al., "Unfoldase-mediated protein translocation through an alpha-hemolysin nanopore," Nat. Biotech., 31: 247-251 (2013).
Olasagasti, F. et al., "Replication of individual DNA molecules under electronic control using a protein nanopore," Nat. Nanotechnol., 5:798-806 (2010).
Pennisi, E., "Genome sequencing. Search for pore-fection," Science 336:534-537 (2012).
Pfeiffer, I., et al., "Bivalent cholesterol-based coupling of oligonucletides to lipid membrane assemblies," J Am Chem Soc 126(33): 10224-10225 (2004).
Ptacek, J. et al., "Global analysis of protein phosphorylation in yeast," Nature, 438:679-684 (2005).
Purnell, R.F., et al., "Discrimination of single base substitutions in a DNA strand immobilized in a biological nanopore," ACS Nano, 3:2533-2538 (2009).
Rodriguez-Larrea, D. et al., "Multistep protein unfolding during nanopore translocation," Nature, 8(4):288-295 (2013).

* cited by examiner

TrxS112:        ...V₉₁GALSKGQLKEFLDANLARRASC₁₁₃

TrxS107:        ...V₉₁GALSKGQLKEFLRRNSAC₁₀₉

TrxS95:         ...V₉₁RRLSKGQLKEFLDANLAC₁₀₉

TrxS107/S112:   ...V₉₁GALSKGQLKEFLRRNSARRASC₁₁₃

TrxA107/S112:   ...V₉₁GALSKGQLKEFLRRNAARRASC₁₁₃

TrxS107/A112:   ...V₉₁GALSKGQLKEFLRRNSARRAAC₁₁₃

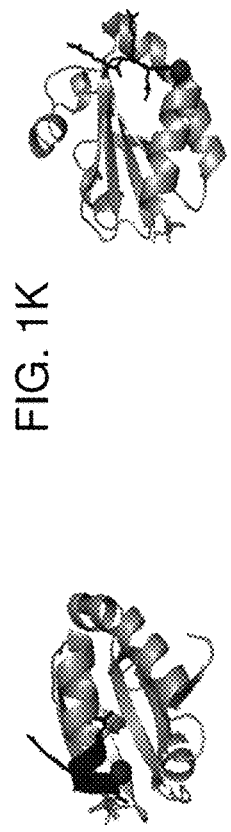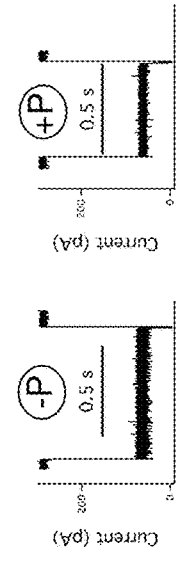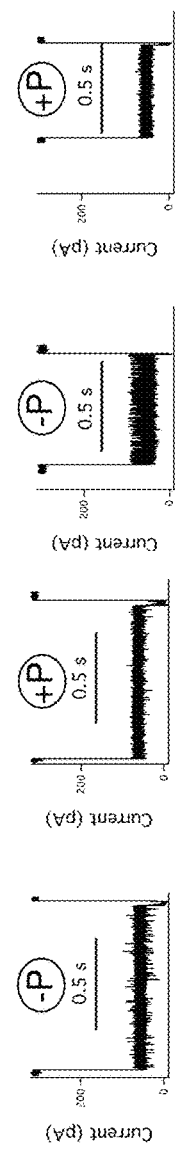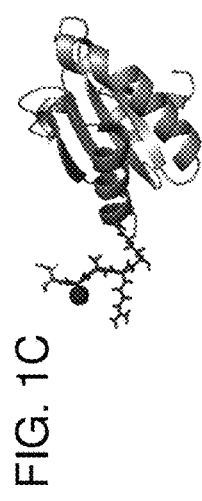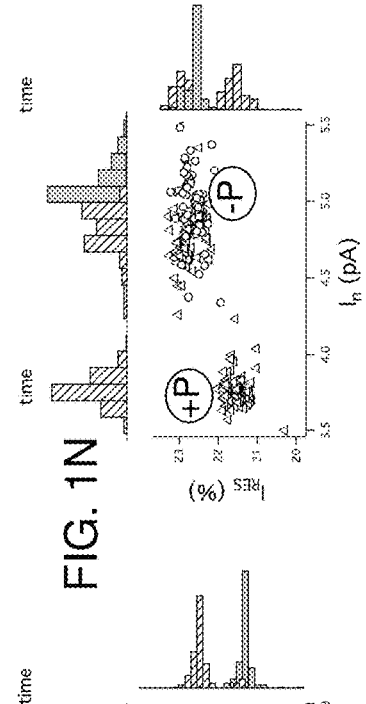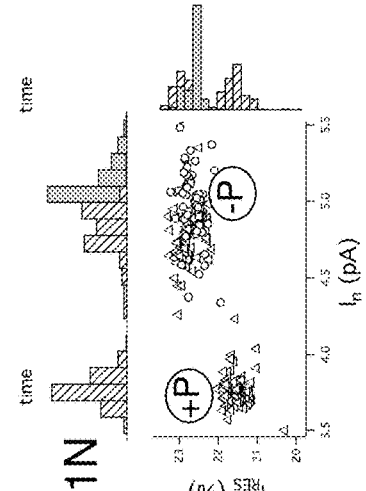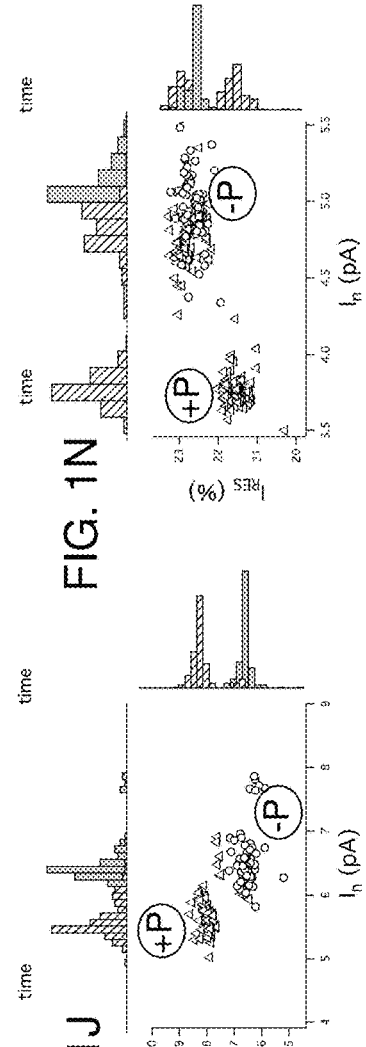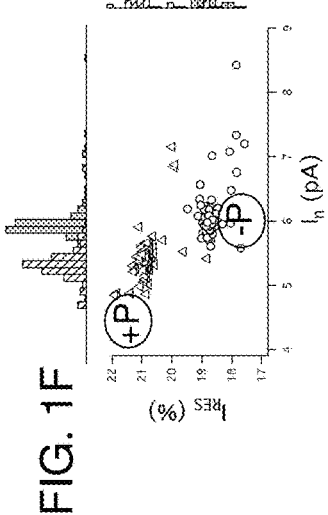
FIG. 1C FIG. 1G FIG. 1K
FIG. 1D FIG. 1E FIG. 1H FIG. 1I FIG. 1L FIG. 1M
FIG. 1F FIG. 1J FIG. 1N

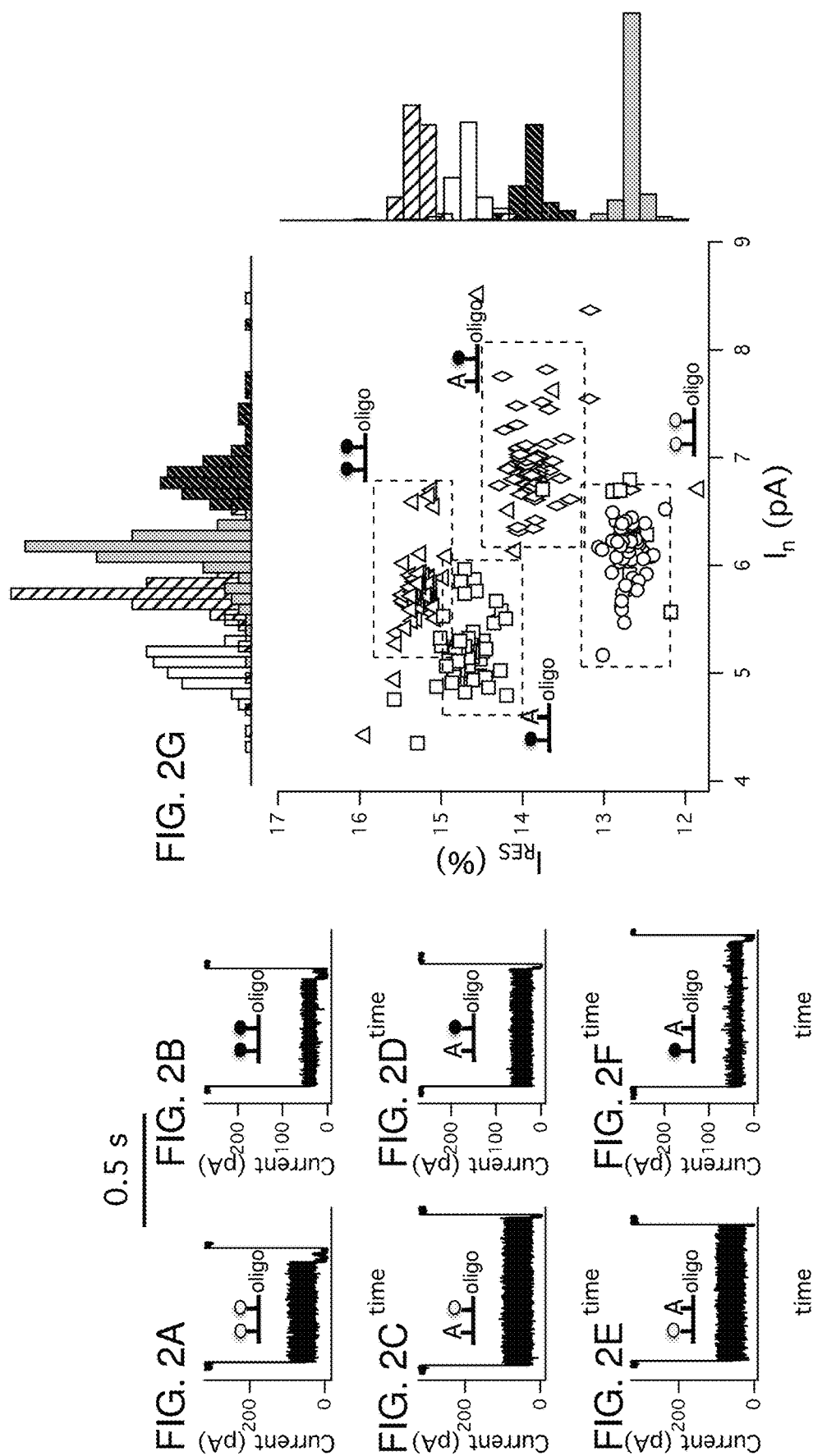

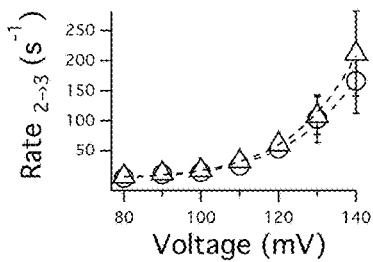 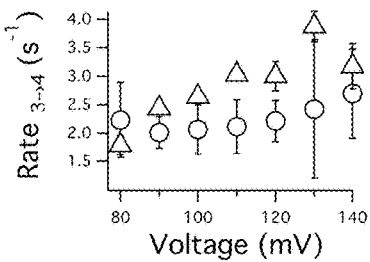 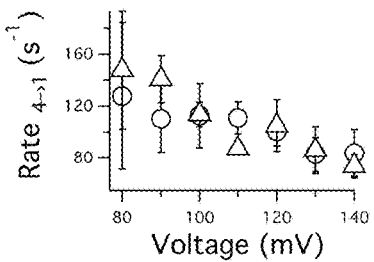
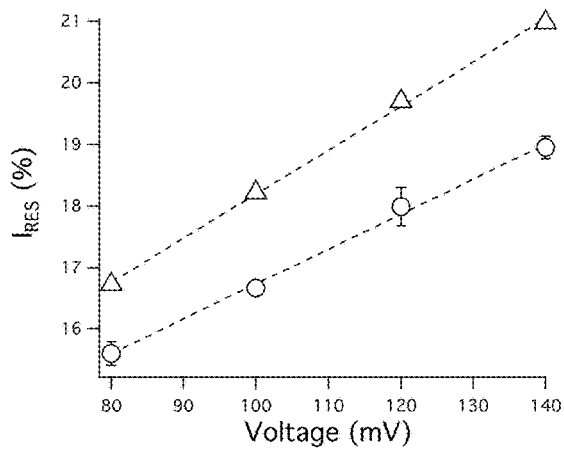 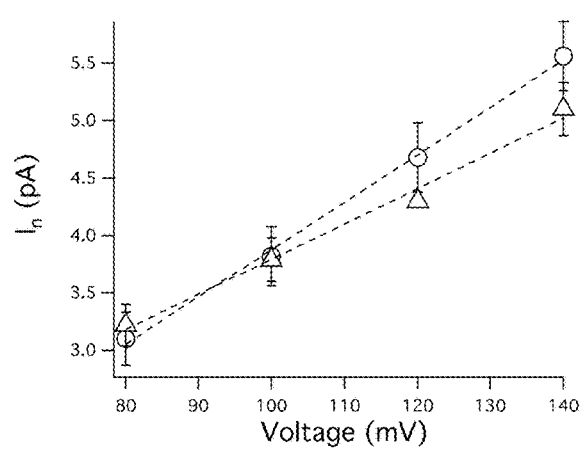

FIG. 13A
FIG. 13B
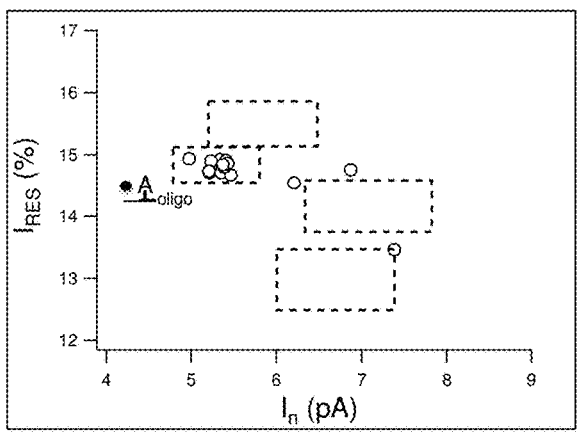
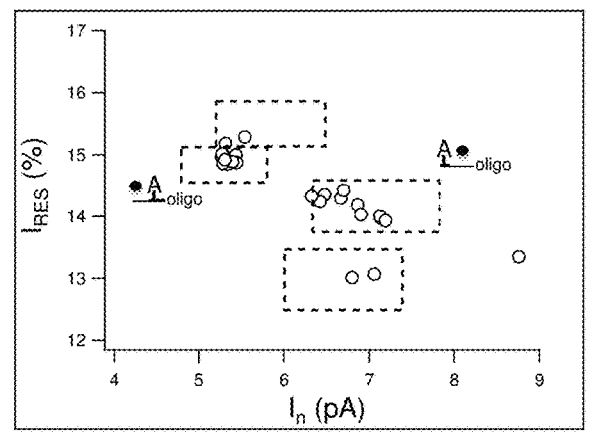
FIG. 13C
FIG. 13D
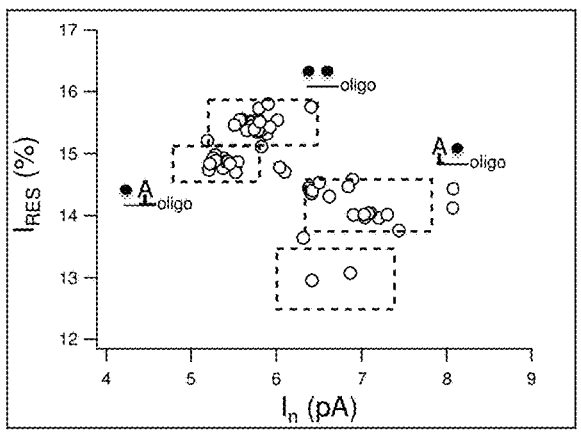
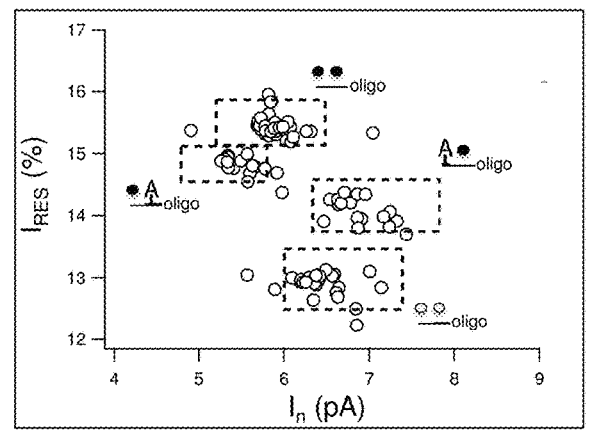

SEQUENCE LISTING

<160> NUMBER OF SEQ ID NOS: 17

<210> SEQ ID NO 1
<211> LENGTH: 882
<212> TYPE: DNA
<213> ORGANISM: Staphylococcus aureus

<400> SEQUENCE: 1

```
atggcagatt ctgatattaa tattaaaacc ggtactacag atattggaag caatactaca      60
gtaaaaacag gtgatttagt cacttatgat aaagaaaatg gcatgcacaa aaaagtattt     120
tatagtttta tcgatgataa aaatcacaat aaaaaactgc tagttattag aacaaaaggt     180
accattgctg tcaatatag agtttatagc gaagaaggtg ctaacaaaag tggtttagcc      240
tggccttcag cctttaaggt acagttgcaa ctacctgata tgaagtagc tcaaatatct      300
gattactatc caagaaattc gattgataca aaagagtata tgagtacttt aacttatgga     360
ttcaacggta atgttactgg tgatgataca ggaaaaattg gcggccttat tggtgcaaat     420
gtttcgattg gtcatacact gaaatatgtt caacctgatt tcaaaacaat tttagagagc     480
ccaactgata aaaagtagg ctggaaagtg atatttaaca atatggtgaa tcaaaattgg     540
ggaccatacg atcgagattc ttggaacccg gtatatggca atcaactttt catgaaaact     600
agaaatggtt ctatgaaagc agcagataac ttccttgatc ctaacaaagc aagttctcta     660
ttatcttcag ggttttcacc agacttcgct acagttatta ctatggatag aaaagcatcc     720
aaacaacaaa caaatataga tgtaatatac gaacgagttc gtgatgatta ccaattgcat     780
tggacttcaa caaattggaa aggtaccaat actaaagata aatggacaga tcgttcttca    840
gaaagatata aaatcgattg ggaaaaagaa gaaatgacaa at                          882
```

<210> SEQ ID NO 2
<211> LENGTH: 293
<212> TYPE: PRT
<213> ORGANISM: Staphylococcus aureus

<400> SEQUENCE: 2

```
Ala Asp Ser Asp Ile Asn Ile Lys Thr Gly Thr Thr Asp Ile Gly Ser
 1               5                  10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
 65                 70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
```

```
              100                 105                 110
Met Ser Thr Leu Thr Tyr Gly Phe Asn Gly Asn Val Thr Gly Asp Asp
            115                 120                 125

Thr Gly Lys Ile Gly Gly Leu Ile Gly Ala Asn Val Ser Ile Gly His
            130                 135             140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
            195                 200             205

Asn Phe Leu Asp Pro Asn Lys Ala Ser Ser Leu Leu Ser Ser Gly Phe
            210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
            275                 280                 285

Glu Glu Met Thr Asn
    290

<210> SEQ ID NO 3
<211> LENGTH: 903
<212> TYPE: DNA
<213> ORGANISM: Staphylococcus aureus

<400> SEQUENCE: 3
atggcggaag gcaaaattac cccggttagc gtgaaaaaag ttgatgacaa agtgaccctg      60
tataaaacga cggcgacggc ggatagcgat aaatttaaaa ttagccagat cctgaccttc     120
aacttcatca agacaaatc ttatgataaa gacaccctgg ttctgaaagc gacgggcaac     180
atcaatagcg ttttgtcaa accgaacccg aatgattacg acttctcaaa actgtattgg     240
ggcgccaaat acaatgtctc gattagctct cagagtaacg attccgtgaa tgcggttgac     300
tatgccccga aaaccaaaa cgaagaattc caggttcaaa cacccctggg ttacacgttc     360
ggcggtgata tttcaatctc gaatggcctg agtggcggtc tgaacggtaa taccgcattt     420
tccgaaacga ttaactataa acaggaaagc taccgtaccc gtctctcgca cacgaattat     480
aaaaacgtcg gctggggtgt ggaagcgcat aaaatcatga atggctgggg tccgtatggc     540
cgtgattcct ttcacccgac ctacggcaac gaactgttcc tggcaggtcg ccagagttcc     600
gcgtatgccg tcaaaatttt tattgctcag catcaaatgc cgctgctgag ccgttctaac     660
tttaatccgg aattcctgtc agtgctgtcg caccgtcagg atcgcgcgaa aaatctaaa     720 atcaccgtta cgtaccagcg tgaaatggac ctgtaccaaa tccgctggaa tggcttctat     780
tgggcaggtg ctaactacaa aaattttaaa acccgcacgt tcaaatctac ctatgaaatc     840
gattgggaaa atcacaaagt caaactgctg acaccaaag aaaccgaaaa caacaaataa     900
taa                                                                  903
```

<210> SEQ ID NO 4
<211> LENGTH: 298
<212> TYPE: PRT
<213> ORGANISM: Staphylococcus aureus

<400> SEQUENCE: 4

Ala Glu Gly Lys Ile Thr Pro Val Ser Val Lys Val Asp Asp Lys
1               5                   10                  15

Val Thr Leu Tyr Lys Thr Thr Ala Thr Ala Asp Ser Asp Lys Phe Lys
        20                  25                  30

Ile Ser Gln Ile Leu Thr Phe Asn Phe Ile Lys Asp Lys Ser Tyr Asp
        35                  40                  45

Lys Asp Thr Leu Val Leu Lys Ala Thr Gly Asn Ile Asn Ser Gly Phe
50                  55                  60

Val Lys Pro Asn Pro Asn Asp Tyr Asp Phe Ser Lys Leu Tyr Trp Gly
65                  70                  75                  80

Ala Lys Tyr Asn Val Ser Ile Ser Ser Gln Ser Asn Asp Ser Val Asn
                85                  90                  95

Ala Val Asp Tyr Ala Pro Lys Asn Gln Asn Glu Phe Gln Val Gln
            100                 105                 110

Asn Thr Leu Gly Tyr Thr Phe Gly Gly Asp Ile Ser Ile Ser Asn Gly
        115                 120                 125

Leu Ser Gly Gly Leu Asn Gly Asn Thr Ala Phe Ser Glu Thr Ile Asn
130                 135                 140

Tyr Lys Gln Glu Ser Tyr Arg Thr Leu Ser Arg Asn Thr Asn Tyr Lys
145                 150                 155                 160

Asn Val Gly Trp Gly Val Glu Ala His Lys Ile Met Asn Gly Trp Gly
                165                 170                 175

Pro Tyr Gly Arg Asp Ser Phe His Pro Thr Tyr Gly Asn Glu Leu Phe
            180                 185                 190

Leu Ala Gly Arg Gln Ser Ser Ala Tyr Ala Gly Gln Asn Phe Ile Ala
        195                 200                 205

Gln His Gln Met Pro Leu Leu Ser Arg Ser Asn Phe Asn Pro Glu Phe
    210                 215                 220

Leu Ser Val Leu Ser His Arg Gln Asp Arg Ala Lys Lys Ser Lys Ile
225                 230                 235                 240

Thr Val Thr Tyr Gln Arg Glu Met Asp Leu Tyr Gln Ile Arg Trp Asn
                245                 250                 255

Gly Phe Tyr Trp Ala Gly Ala Asn Tyr Lys Asn Phe Lys Thr Arg Thr
            260                 265                 270

Phe Lys Ser Thr Tyr Glu Ile Asp Trp Glu Asn His Lys Val Lys Leu
        275                 280                 285

Leu Asp Thr Lys Glu Thr Glu Asn Asn Lys
    290                 295

<210> SEQ ID NO 5
<211> LENGTH: 849
<212> TYPE: DNA
<213> ORGANISM: Staphylococcus aureus

<400> SEQUENCE: 5
atggaaaaca aaatcgaaga catcggtcaa ggcgctgaaa tcatcaaacg cacgcaggac      60
attacctcta acgtctggc tattacccag aatattcaat tcgatttcgt gaaagacaaa     120
aaatacaaca aagatgcact ggtggttaaa atgcagggct ttatcagctc tcgtaccacg     180
tacagcgatc tgaaaaaata tccgtacatt aaacgcatga tctggccgtt ccagtacaac     240

```
attagtctga aaaccaaaga ttccaacgtg gacctgatta attacctgcc gaaaaacaaa      300
atcgatagtg cggacgtttc ccagaaactg ggctataaca ttggcggtaa ttttcaatca      360
gccccgtcga tcggcggtag tggttccttc aattactcaa aaaccatctc gtacaaccag      420
aaaaattacg ttacggaagt cgaaagccaa aactctaaag gcgtgaaatg gggtgttaaa      480
gcgaattcat ttgtcacccc gaacggccag gtgtcggcgt atgatcagta cctgtttgca      540
caagacccga cgggtccggc agcacgtgat tatttcgttc cggacaatca gctgccgccg      600
ctgattcaaa gcggctttaa cccgtctttc atcaccacgc tgtcccatga acgtggcaaa      660
ggtgataaaa gcgaatttga aattacctat ggtcgcaaca tggatgcaac ctatgcttac      720
gttacgcgtc atcgcctggc agtcgatcgt aaacacgacg ctttcaaaaa ccgcaatgtc      780
accgtgaaat acgaagtcaa ctggaaaacg cacgaagtca aatcaaaag tatcacgccg      840 aaataataa                                                              849
```

<210> SEQ ID NO 6
<211> LENGTH: 280
<212> TYPE: PRT
<213> ORGANISM: Staphylococcus aureus

<400> SEQUENCE: 6

```
Glu Asn Lys Ile Glu Asp Ile Gly Gln Gly Ala Glu Ile Ile Lys Arg
1               5                   10                  15

Thr Gln Asp Ile Thr Ser Lys Arg Leu Ala Ile Thr Gln Asn Ile Gln
            20                  25                  30

Phe Asp Phe Val Lys Asp Lys Lys Tyr Asn Lys Asp Ala Leu Val Val
        35                  40                  45

Lys Met Gln Gly Phe Ile Ser Ser Arg Thr Thr Tyr Ser Asp Leu Lys
    50                  55                  60

Lys Tyr Pro Tyr Ile Lys Arg Met Ile Trp Pro Phe Gln Tyr Asn Ile
65                  70                  75                  80

Ser Leu Lys Thr Lys Asp Ser Asn Val Asp Leu Ile Asn Tyr Leu Pro
                85                  90                  95

Lys Asn Lys Ile Asp Ser Ala Asp Val Ser Gln Lys Leu Gly Tyr Asn
            100                 105                 110

Ile Gly Gly Asn Phe Gln Ser Ala Pro Ser Ile Gly Gly Ser Gly Ser
        115                 120                 125

Phe Asn Tyr Ser Lys Thr Ile Ser Tyr Asn Gln Lys Asn Tyr Val Thr
    130                 135                 140

Glu Val Glu Ser Gln Asn Ser Lys Gly Val Lys Trp Gly Val Lys Ala
145                 150                 155                 160

Asn Ser Phe Val Thr Pro Asn Gly Gln Val Ser Ala Tyr Asp Gln Tyr
                165                 170                 175

Leu Phe Ala Gln Asp Pro Thr Gly Pro Ala Ala Arg Asp Tyr Phe Val
            180                 185                 190

Pro Asp Asn Gln Leu Pro Pro Leu Ile Gln Ser Gly Phe Asn Pro Ser
        195                 200                 205

Phe Ile Thr Thr Leu Ser His Glu Arg Gly Lys Gly Asp Lys Ser Glu
    210                 215                 220

Phe Glu Ile Thr Tyr Gly Arg Asn Met Asp Ala Thr Tyr Ala Tyr Val
225                 230                 235                 240

Thr Arg His Arg Leu Ala Val Asp Arg Lys His Asp Ala Phe Lys Asn
                245                 250                 255
```

```
Arg Asn Val Thr Val Lys Tyr Glu Val Asn Trp Lys Thr His Glu Val
                260                 265                 270

Lys Ile Lys Ser Ile Thr Pro Lys
            275                 280

<210> SEQ ID NO 7
<211> LENGTH: 558
<212> TYPE: DNA
<213> ORGANISM: Artificial sequence
<220> FEATURE:
<223> OTHER INFORMATION: MS-B1 mutant MspA monomer

<400> SEQUENCE: 7
atgggtctgg ataatgaact gagcctggtg gacggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc aacaatggta acattaccgc accgccgttt     300
ggcctgaaca gcgtgattac gccgaacctg tttccgggtg ttagcatctc tgcccgtctg     360
ggcaatggtc cgggcattca agaagtggca acctttagtg tgcgcgtttc cggcgctaaa     420
ggcggtgtcg cggtgtctaa cgcccacggt accgttacgg gcgcggccgg cggtgtcctg     480
ctgcgtccgt tcgcgcgcct gattgcctct accggcgaca cgttacgac ctatggcgaa     540 ccgtggaata tgaactaa                                                   558

<210> SEQ ID NO 8
<211> LENGTH: 184
<212> TYPE: PRT
<213> ORGANISM: Artificial sequence
<220> FEATURE:
<223> OTHER INFORMATION: MS-B1 mutant MspA monomer

<400> SEQUENCE: 8

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175
```

Tyr Gly Glu Pro Trp Asn Met Asn
            180

<210> SEQ ID NO 9
<211> LENGTH: 184
<212> TYPE: PRT
<213> ORGANISM: Mycobacterium smegmatis

<400> SEQUENCE: 9

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 10
<211> LENGTH: 184
<212> TYPE: PRT
<213> ORGANISM: Mycobacterium smegmatis

<400> SEQUENCE: 10

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

```
Ala Thr Phe Ser Val Asp Val Ser Gly Pro Ala Gly Gly Val Ala Val
        130                 135                 140

Ser Asn Ala His Gly Thr Val Thr Gly Ala Ala Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 11
<211> LENGTH: 183
<212> TYPE: PRT
<213> ORGANISM: Mycobacterium smegmatis

<400> SEQUENCE: 11

Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
            20                  25                  30

Asn Arg Leu Thr Arg Glu Trp Phe His Ser Gly Arg Ala Thr Tyr His
        35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Asp Ile Thr Gln Pro
                85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
        115                 120                 125

Thr Phe Ser Val Asp Val Lys Gly Ala Lys Gly Ala Val Ala Val Ser
    130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180

<210> SEQ ID NO 12
<211> LENGTH: 23
<212> TYPE: PRT
<213> ORGANISM: Artificial sequence
<220> FEATURE:
<223> OTHER INFORMATION: C terminus Trx mutant

<400> SEQUENCE: 12

Val Gly Ala Leu Ser Lys Gly Gln Leu Lys Glu Phe Leu Asp Ala Asn
1               5                   10                  15

Leu Ala Arg Arg Ala Ser Cys
            20

<210> SEQ ID NO 13
<211> LENGTH: 19
<212> TYPE: PRT
<213> ORGANISM: Artificial sequence
<220> FEATURE:
<223> OTHER INFORMATION: C terminus Trx mutant
```

```
<400> SEQUENCE: 13

Val Gly Ala Leu Ser Lys Gly Gln Leu Lys Glu Phe Leu Arg Arg Asn
1               5                   10                  15

Ser Ala Cys

<210> SEQ ID NO 14
<211> LENGTH: 19
<212> TYPE: PRT
<213> ORGANISM: Artificial sequence
<220> FEATURE:
<223> OTHER INFORMATION: C terminus Trx mutant

<400> SEQUENCE: 14

Val Arg Arg Leu Ser Lys Gly Gln Leu Lys Glu Phe Leu Asp Ala Asn
1               5                   10                  15

Leu Ala Cys

<210> SEQ ID NO 15
<211> LENGTH: 23
<212> TYPE: PRT
<213> ORGANISM: Artificial sequence
<220> FEATURE:
<223> OTHER INFORMATION: C terminus Trx mutant

<400> SEQUENCE: 15

Val Gly Ala Leu Ser Lys Gly Gln Leu Lys Glu Phe Leu Arg Arg Asn
1               5                   10                  15

Ser Ala Arg Arg Ala Ser Cys
            20

<210> SEQ ID NO 16
<211> LENGTH: 23
<212> TYPE: PRT
<213> ORGANISM: Artificial sequence
<220> FEATURE:
<223> OTHER INFORMATION: C terminus Trx mutant

<400> SEQUENCE: 16

Val Gly Ala Leu Ser Lys Gly Gln Leu Lys Glu Phe Leu Arg Arg Asn
1               5                   10                  15

Ala Ala Arg Arg Ala Ser Cys
            20

<210> SEQ ID NO 17
<211> LENGTH: 23
<212> TYPE: PRT
<213> ORGANISM: Artificial sequence
<220> FEATURE:
<223> OTHER INFORMATION: C terminus Trx mutant

<400> SEQUENCE: 17

Val Gly Ala Leu Ser Lys Gly Gln Leu Lys Glu Phe Leu Arg Arg Asn
1               5                   10                  15

Ser Ala Arg Arg Ala Ala Cys
            20
```

METHOD OF ANALYZING POST-TRANSLATIONAL MODIFICATIONS

CROSS REFERENCE TO RELATED APPLICATIONS

This application is a continuation of U.S. patent application Ser. No. 15/023,652, filed Mar. 21, 2016 (now U.S. Pat. No. 10,712,254), which is a 35 U.S.C. 371 national stage filing of International Application No. PCT/GB2014/052873, filed on Sep. 22, 2014, which claims priority to United Kingdom Patent Application No. 1316849.7, filed on Sep. 23, 2013, and to U.S. Provisional Application No. 61/896,933, filed on Oct. 29, 2013. The contents of the aforementioned applications are hereby incorporated by reference in their entireties.

GOVERNMENT LICENSE RIGHTS

This invention was made with government support under Grant No. R01 HG003709 awarded by National Institutes of Health. The government has certain rights in the invention. The work leading to this invention has also received funding from the European Research Council under the European Union's Seventh Framework programme (FP7/2007-2013)/ ERC grant agreement no. 294443.

SEQUENCE LISTING

The instant application contains a Sequence Listing which has been submitted electronically in ASCII format and is hereby incorporated by reference in its entirety. Said ASCII copy, created on May 27, 2020, is named JKJ_054USCN_Sequence_Listing.txt and is 21,242 bytes in size.

FIELD OF THE INVENTION

The invention relates to a new method of determining the presence, absence, number or position(s) of one or more post-translational modifications (PTMs) in a peptide, polypeptide or protein. The invention uses transmembrane pores.

BACKGROUND OF THE INVENTION

The functional properties of most proteins are regulated by post-translational modifications (PTM) of specific residues. Up to now, phosphorylation at serine, threonine or tyrosine is the most frequent experimentally determined PTM[1] (http://selene.princeton.edu/PTMCuration). In eukaryotes, 30% (*S. cerevisiae*) to 50% (mouse) of protein species are phosphorylated[2,3]. Proteins of critical importance may have multiple phosphorylation sites, serving to activate or inactivate a protein, promote its degradation, or modulate interactions with protein partners[4]. For example, p53 has at least 18 phosphorylation sites[4,5]. Importantly, multi-site modifications can occur in different combinations, leading to different functional forms of a protein[6].

Early studies of protein phosphorylation relied on 2D gel electrophoresis, which is based on changes in protein electrophoretic mobility and isoelectric point caused by the incorporation of phosphate groups[7]. 2D gel electrophoresis cannot resolve different phosphorylation sites within the same protein[8,9]. Recently, mass spectrometry (MS) of the phosphoproteome has come to the fore for studies of phosphorylation in vivo. Through the use of protease digestion and high-resolution MS, thousands of phosphoprotein species can be identified[9,10]. When samples from different sources (e.g. treated and control) are differentially labelled with isotopes, changes in the levels of phosphorylation at specific sites in specific proteins can be estimated[11]. Despite these advances, the determination of patterns of phosphorylation within individual protein molecules remains challenging[2]. For example, proteins monophosphorylated on one of two adjacent sites are difficult to distinguish. The occupancy and connectivity of phosphorylation sites is a problem ideally suited for single-molecule approaches.

Engineered protein nanopores have been used for the stochastic detection of a wide variety of molecules in solution[12,13], ranging from divalent metal cations[14] to organic molecules[15] to chemically reactive substances[16]. Nanopore technology has also been investigated as an ultra-rapid, low-cost platform for single-molecule sequencing of DNA and RNA[17,18]. For example, single-stranded DNA can be ratcheted through protein pores with enzymes[19-22] and the sequence read[23-27] from base-dependent transitions in the ionic current[28-31].

SUMMARY OF THE INVENTION

The inventors have surprisingly demonstrated that PTMs can be detected at the single-molecule level through alterations in the current signature through nanopores. Remarkably, modification at different locations in the protein result in different signatures, which allows rapid discrimination between sites of modification. The inventors have also surprisingly shown that the modification states of two adjacent sites (separated by one residue) can be distinguished and quantified: namely, the unmodified state, the two mono-modified states, and the doubly modified state.

Accordingly, the invention provides a method for determining the presence, absence, number or position(s) of one or more PTMs in a peptide, polypeptide or protein, the method comprising:

(a) contacting the peptide, polypeptide or protein with a transmembrane pore such that the peptide, polypeptide or protein moves through the pore; and (b) taking one or more current measurements as the peptide, polypeptide or protein moves with respect to the pore and thereby determining the presence, absence, number or position(s) of one or more PTMs in the peptide, polypeptide or protein.

The invention also provides a method of determining whether or not an organism has a disease, disorder or phenotype associated with one or more PTMs of a peptide, polypeptide or protein, the method comprising:

(a) carrying out a method of the invention on a sample from the organism comprising the peptide, polypeptide or protein; and (b) determining whether or not one or more PTMs of the peptide, polypeptide or protein are present and thereby determining whether or not the organism has the disease, disorder or phenotype.

DESCRIPTION OF THE FIGURES

FIGS. 1A-1N show single-molecule nanopore detection of phosphorylation at different sites in a model substrate. (FIG. 1A) Current signature of the unfolding and translocation of TrxS112$^{-P}$-oligo(dC)$_{30}$ through an αHL pore showing the four characteristic levels: level 1, open pore; level 2, oligonucleotide leader threaded into the pore; level 3, C terminus of the protein substrate in the pore; level 4, unfolding of the remainder of the protein and diffusion through the pore. (FIG. 1B) Sequences of the C termini of Trx mutants used in this work. Phosphorylation sites are denoted with an enlarged S (Ser). In two mutants, the phosphorylatable Ser residues have been replaced with Ala (A). (FIG. 1C) Molecular model of TrxS112$^{-P}$, which features a PKA phosphorylation site on a C terminal extension (blue sticks). The side chain O atom of Ser-112 is shown as a round ball. (FIG. 1D) Current signature of TrxS112$^{-P}$-oligo(dC)$_{30}$. (FIG. 1E) Current signature of TrxS112$^{+P}$-oligo(dC)$_{30}$. (FIG. 1F) Representative 2D scatter plot of the residual current ($I_{RES\ \%}$) and noise ($I_n$) in level 3 of TrxS112$^{-P}$-oligo(dC)$_{30}$ and TrxS112$^{+P}$-oligo(dC)$_{30}$ and the associated histograms (200 events were recorded). (FIG. 1G) Molecular model of TrxS107$^{-P}$, which features a PKA phosphorylation site on the C-terminal α-helix (blue). The side chain O atom of Ser-107 is shown as a round ball. (FIG. 1H) Current signature of TrxS107$^{-P}$-oligo(dC)$_{30}$. (FIG. 1I) Current signature of TrxS107$^{+P}$-oligo(dC)$_{30}$. (FIG. 1J) Representative 2D scatter plot of the residual current ($I_{RES\ \%}$) and noise ($I_n$) in level 3 of TrxS107$^{-P}$-oligo(dC)$_{30}$ and TrxS107$^{+P}$-oligo(dC)$_{30}$ and the associated histograms (199 events were recorded). (FIG. 1K) Molecular model of TrxS95$^{-P}$, which features a PKA phosphorylation site in the loop that precedes the C-terminal helix (blue sticks). The side chain O atom of Ser-95 is shown as a round ball. (FIG. 1L) Current signature of TrxS95$^{-P}$-oligo(dC)$_{30}$. (FIG. 1M) Current signature of TrxS95$^{+P}$-oligo(dC)$_{30}$. (FIG. 1N) Representative 2D scatter plot of the residual current ($I_{RES\ \%}$) and noise (L) in level 3 of TrxS95$^{-P}$-oligo(dC)$_{30}$ and TrxS95$^{+P}$-oligo(dC)$_{30}$ and the associated histograms (250 events were recorded). All measurements were done at +140 mV. The experiments in (FIG. 1F), (FIG. 1J) and (FIG. 1N) were repeated three times.

FIGS. 2A-2G show single-molecule nanopore detection of four phosphorylation states. (FIG. 2A) Representative ionic current trace for TrxS107$^{-P}$/S112$^{-P}$-oligo(dC)$_{30}$. (FIG. 2B) Trace for TrxS107$^{+P}$/S112$^{+P}$-oligo(dC)$_{30}$. (FIG. 2C) Trace for TrxA107/S112$^{-P}$-oligo(dC)$_{30}$. (FIG. 2D) Trace for TrxA107/S112$^{+P}$-oligo(dC)$_{30}$. (FIG. 2E) Trace for TrxS107$^{-P}$/A112-oligo(dC)$_{30}$. (FIG. 2F) Trace for TrxS107$^{+P}$/A112-oligo(dC)$_{30}$. (FIG. 2G) Representative 2D scatter plot of the residual currents ($I_{RES\ \%}$) and noise (L) in level 3 and the associated histograms for four possible phosphorylation states (as denoted by symbols in FIGS. 2A, 2B, 2D, and 2F: TrxS107$^{+P}$/S112$^{+P}$-oligo(dC)$_{30}$, TrxA107/S112$^{+P}$-oligo(dC)$_{30}$, TrxS107$^{+P}$/A112-oligo(dC)$_{30}$ and TrxS107$^{-P}$/S112$^{-P}$-oligo(dC)$_{30}$. In FIG. 2G, the same pore was used throughout and the cis compartment perfused before the addition of each Trx variant, 342 events were recorded in total and a few events (<8%) may be due to carry over because incomplete perfusion. The ability of the same pore to distinguish the 4 constructs was verified twice. All measurements were done at +140 mV.

(FIG. 4A) Representative current trace with 4 levels at +140 mV. (FIG. 4B) Molecular model of the thioredoxin mutant TrxS112$^{-P}$ showing the PKA recognition sequence (blue sticks) and the phosphorylation site (round ball). (FIG. 4C) Voltage dependence of the rate of step 2 to 3, (O) V5-C109-oligo(dC)$_{30}$$^{37}$; (□) TrxS112$^{-13}$-oligo(dC)$_{30}$. (FIG. 4D) Voltage dependence of the rate of step 3 to 4, (O) V5-C109-oligo(dC)$_{30}$$^{37}$; (□) TrxS112$^{-P}$-oligo(dC)$_{30}$. (FIG. 4E) Voltage dependence of the rate of step 4 to 1, (O) V5-C109-oligo(dC)$_{30}$$^{37}$; (□) TrxS112$^{-P}$-oligo(dC)$_{30}$. Error bars represent the standard deviation between independent experiments, each using a different pore (n=3).

(FIG. 5A) TrxS112$^{-P}$ (expected mass 12202). (FIG. 5B) TrxS107$^{-P}$ (expected mass 11832). (FIG. 5C) TrxS95$^{-P}$ (expected mass 11916). (FIG. 5D) TrxS112$^{+P}$. (FIG. 5E) TrxS107$^{+P}$. (FIG. 5F) TrxS95$^{+P}$. The expected mass gain after phosphorylation is 80 Da. Note that (FIG. 5E) and (FIG. 5F) contain peaks for the non-phosphorylated protein.

FIGS. 6A-6C show the voltage dependence of the co-translocational unfolding of Trx112$^{+P}$-oligo(dC)$_{30}$ within the αHL pore. (FIG. 6A) Voltage dependence of the rate of step 2 to 3, (O) Trx112$^{-P}$-oligo(dC)$_{30}$; (Δ) Trx112$^{+P}$-oligo(dC)$_{30}$. (FIG. 6B) Voltage dependence of the rate of step 3 to 4, (O) Trx112$^{-P}$-oligo(dC)$_{30}$; (Δ) Trx112$^{+P}$-oligo(dC)$_{30}$. (FIG. 6C) Voltage dependence of the rate of step 4 to 1, (O) Trx112$^{-P}$-oligo(dC)$_{30}$; (Δ) Trx112$^{+P}$-oligo(dC)$_{30}$. Error bars represent the standard deviations between independent experiments, each with a different pore, each with a different pore (n=3).

FIGS. 7A and 7B show the voltage-dependences of the residual current ($I_{RES\ \%}$) and noise ($I_n$) of level 3. (FIG. 7A) Residual current ($I_{RES\ \%}$) of level 3 as a function of the applied voltage, (O) Trx112$^{-P}$-oligo(dC)$_{30}$, (Δ) Trx112$^{+P}$-oligo(dC)$_{30}$. (FIG. 7B) Noise ($I_n$) as a function of voltage. $I_n$ is the standard deviation of a Gaussian fit to an all-points histogram of the ionic current in level 3. (O) Trx112$^{-P}$-oligo(dC)$_{30}$, (Δ) Trx112$^{+P}$-oligo(dC)$_{30}$. Error bars represent the standard deviations between independent experiments, each with a different pore (n=3).

(FIG. 8A) Voltage dependences of the rates of step 2 to 3, (□) Trx107$^{-P}$-oligo(dC)$_{30}$; (Δ) Trx107$^{+P}$-oligo(dC)$_{30}$; (O) Trx112$^{-P}$-oligo(dC)$_{30}$. (FIG. 8B) Voltage dependences of the rates of step 3 to 4, (□) Trx107$^{-P}$-oligo(dC)$_{30}$; (Δ) Trx107$^{+13}$-oligo(dC)$_{30}$; (O) Trx112$^{-P}$-oligo(dC)$_{30}$. (FIG. 8C) Voltage dependences of the rates of step 4 to 1, (□) Trx107$^{-P}$-oligo(dC)$_{30}$; (Δ) Trx107$^{+P}$-oligo(dC)$_{30}$; (O) Trx112$^{-P}$-oligo(dC)$_{30}$. (FIG. 8D) Voltage dependences of step 2 to 3, (□) Trx95$^{-P}$-oligo(dC)$_{30}$; (O) Trx112$^{-P}$-oligo(dC)$_{30}$. (FIG. 8E) Voltage dependences of the rates of step 3 to 4, (□) Trx95$^{-P}$-oligo(dC)$_{30}$; (O) Trx112$^{-P}$-oligo(dC)$_{30}$. (FIG. 8F) Voltage dependences of the rates of step 4 to 1, (□) Trx95$^{-P}$-oligo(dC)$_{30}$; (O) Trx112$^{-P}$-oligo(dC)$_{30}$. Error bars represent the standard deviations between independent experiments, each with a different pore (n=3).

10 for a zoom out). Each construct was further analyzed in 3 independent experiments, each for a different pore.

Figure 9:
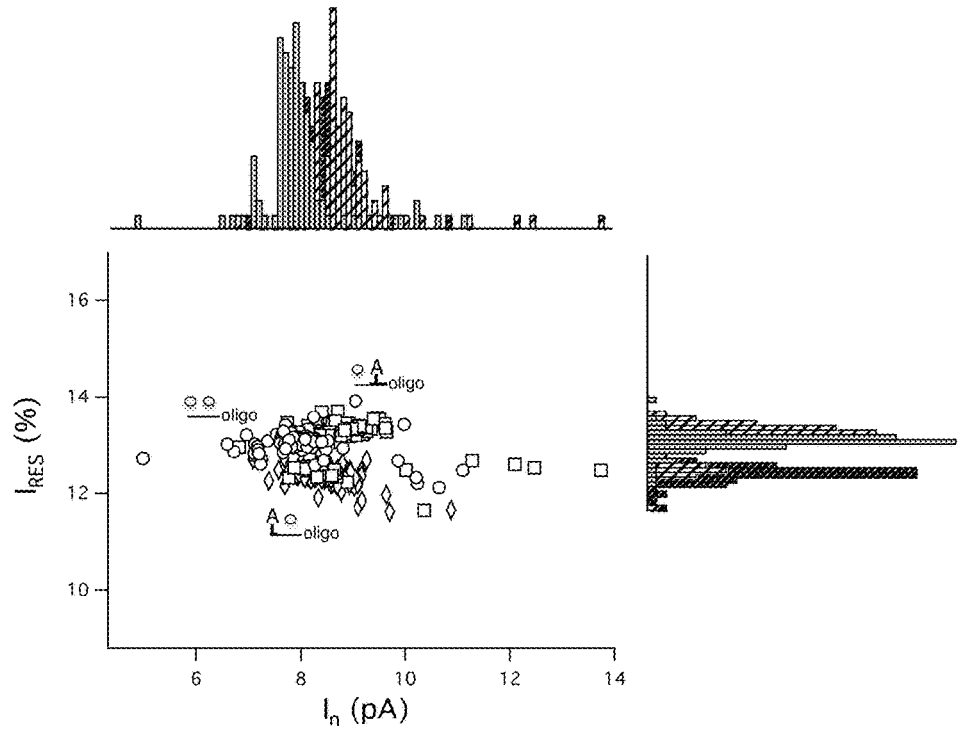
FIG. 9 shows a 2D plot of residual currents ($I_{RES\ \%}$) and noise ($I_n$) and associated histograms for (O) TrxS107$^{-P}$/S112$^{-P}$-oligo(dC)$_{30}$, (□) TrxA107/S112$^{-P}$-oligo(dC)$_{30}$ and (◊) TrxS107$^{-P}$/A112-oligo(dC)$_{30}$. All three constructs were examined with the same αHL pore (the cis compartment was perfused before the addition of each Trx variant) at +140 mV, analyzing 300 events in total. The high conductivity sub-states of level 3 are not included in this figure (see FIG.
Figure 10:
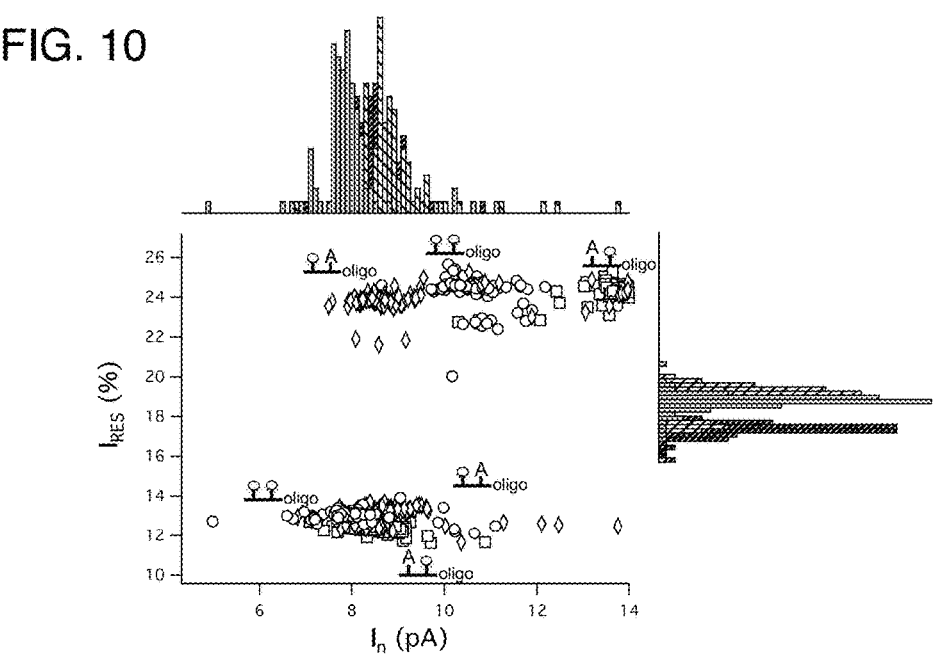
Figure 11A:
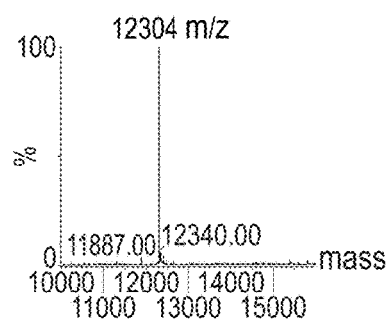
Figure 11B:
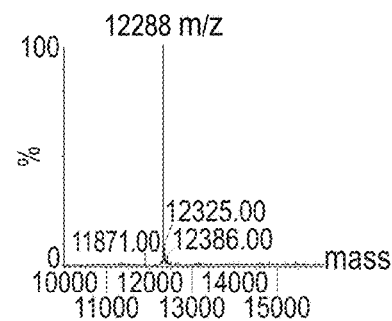
Figure 11C:
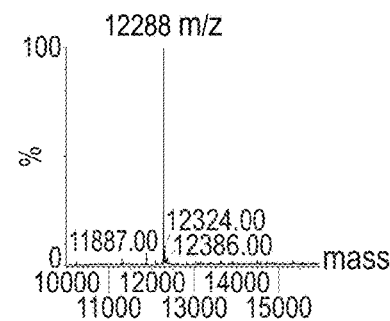
Figure 11D:
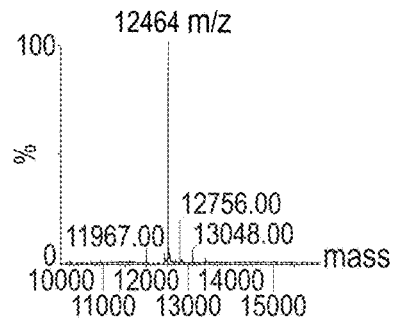
Figure 11E:
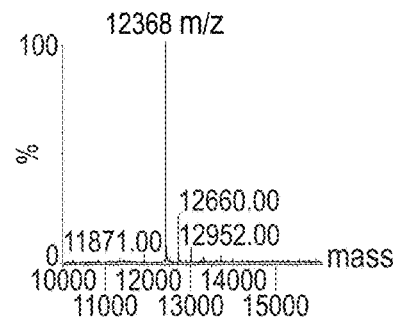
Figure 11F:
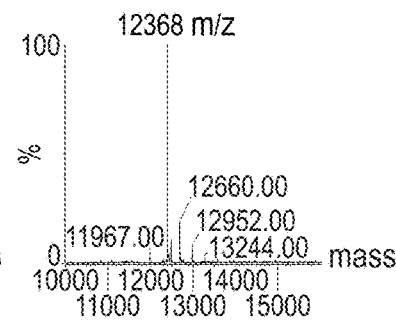

FIG. 10 shows a zoom out of FIG. 9. 2D plot of residual current ($I_{RES\ \%}$) and noise (Is) for (O) TrxS107$^{-P}$/S112$^{-P}$-oligo(dC)$_{30}$, (□) TrxA107/S112$^{-P}$-oligo(dC)$_{30}$ and (Q) TrxS107$^{-P}$/A112-oligo(dC)$_{30}$. All three constructs were examined with the same WT αHL pore (the cis compartment was perfused before the addition of each Trx variant) at +140 mV, analyzing 300 events in total. The sub-states of higher conductance are observed at $I_{RES\ \%}$ values of approximately 24% of the open pore value (Jo). Each construct was further analyzed in 3 independent experiments, each with a different pore.

FIGS. 11A-11F show ESI LC-MS in positive ion mode before and after phosphorylation of constructs TrxS107/S112, TrxA107/S112 and TrxS107/A112 (deconvoluted spectra). (FIG. 11A) TrxS107$^{-P}$/S112$^{-P}$ (expected mass 12303). (FIG. 11B) TrxA107/S112$^{-P}$ (expected mass 12287). (FIG. 11C) TrxS107$^{-P}$/A112 (expected mass 12287). (FIG. 11D) TrxS107$^{+P}$/S112$^{+P}$. (FIG. 11E) TrxA107/S112$^{+P}$. (FIG. 11F) TrxA107/S112$^{+P}$. The expected mass gain after phosphorylation at one site is 80 Da.

Figure 12:
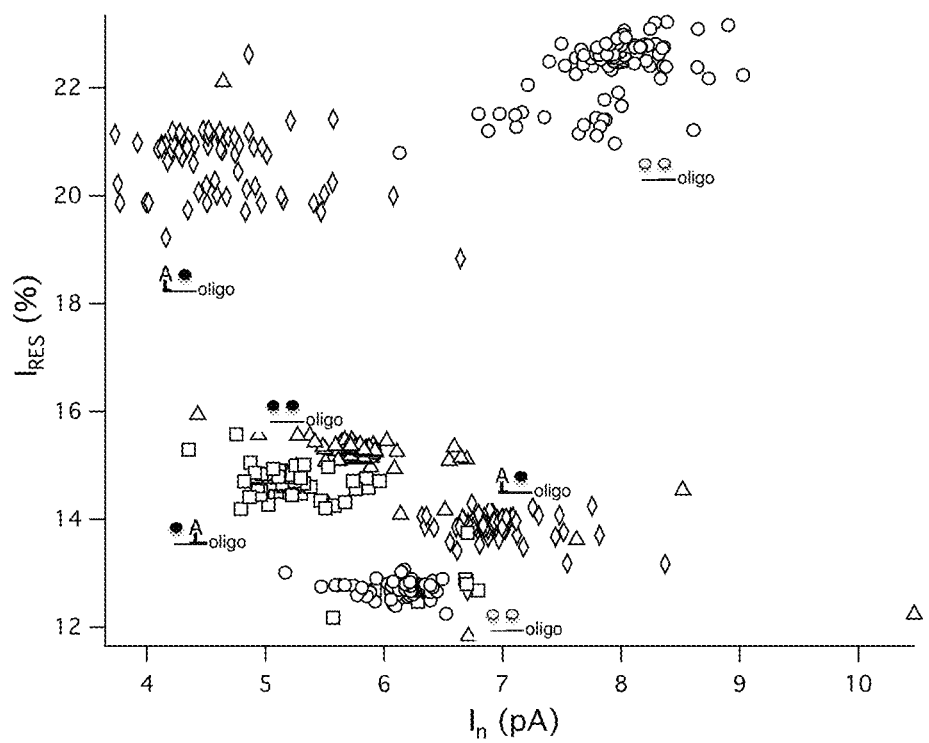

FIG. 12 shows a zoom-out of a 2D plot of residual currents ($I_{RES\ \%}$) versus noise (L) from FIG. 2. (Δ) TrxS107$^{+P}$/S112$^{+P}$-oligo(dC)$_{30}$, (□) TrxA107/S112$^{+P}$-oligo (dC)$_{30}$, (O) TrxS107$^{+P}$/A112-oligo(dC)$_{30}$, and (O) TrxS107$^{-P}$/S112$^{-P}$-oligo(dC)$_{30}$. All the measurements were done with the same WT αHL pore (the cis compartment was perfused before the addition of each Trx variant) at +140 mV and involved the measurement of a total of 342 events a few events may be due to carry over because incomplete perfusion (<8%). The sub-states of higher conductance are observed at $I_{RES\ \%}$ values of approximately 21 to 22% of the open pore value (Jo). Each construct was further analyzed in 3 independent experiments, each with a different pore.

Figure 3:
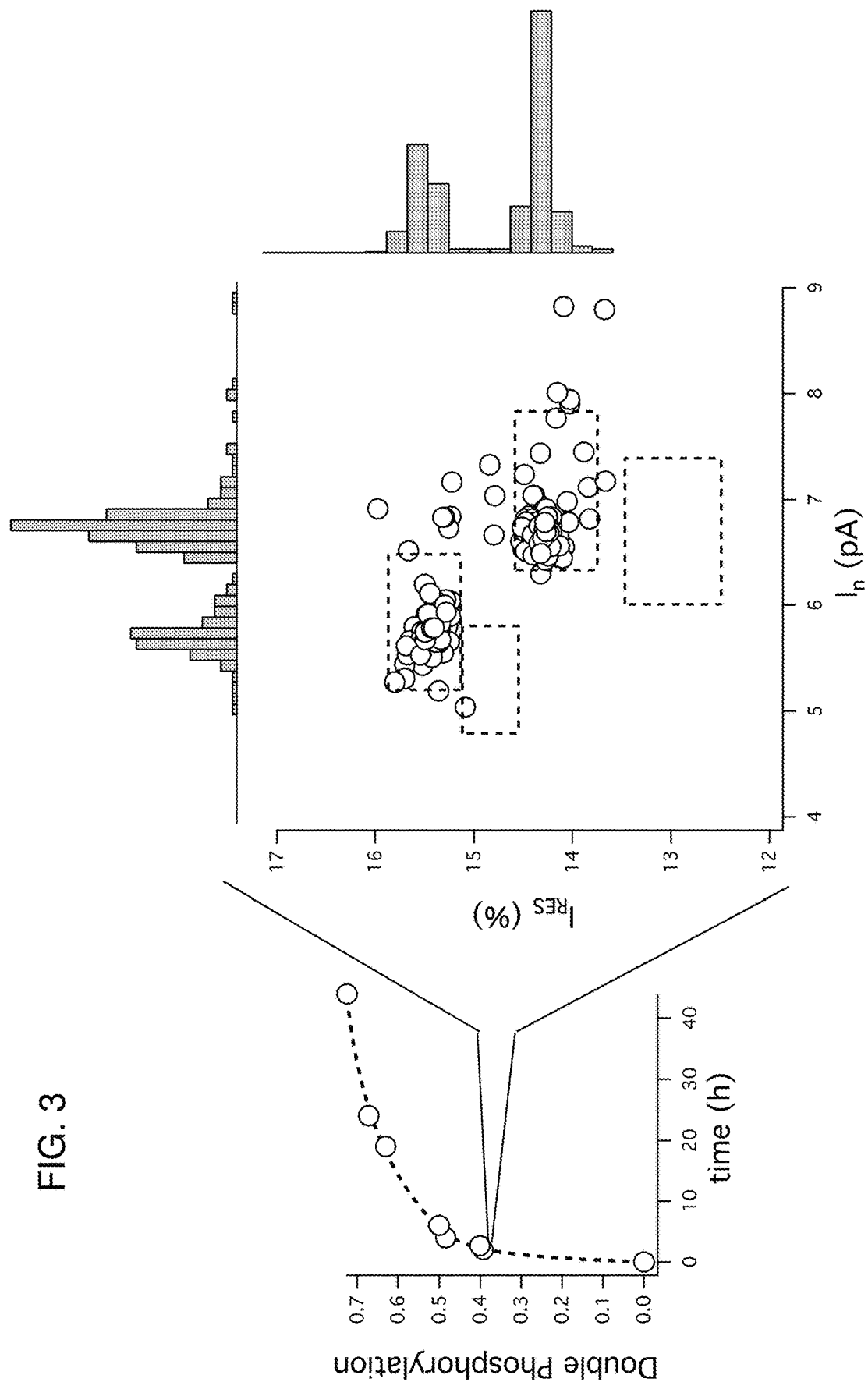
FIG. 3 shows single-molecule nanopore detection of a sample containing a mixture of phosphorylation states. Time dependence of phosphorylation of TrxS107$^{-P}$/S112$^{-P}$. The fraction of the protein converted to the doubly phosphorylated TrxS107$^{+P}$/S112$^{+P}$ as determined by IEF is shown. Representative 2D scatter plot of the residual currents ($I_{RES\ \%}$) and noise (L) in level 3 and the associated histograms after 2 h of phosphorylation, followed by conjugation to oligo(dC)$_{30}$ and αHL nanopore analysis (202 events were recorded) at +140 mV. The ability of the same pore to distinguish the mixture was verified twice. The boxes delimit the same areas displayed in FIG. 13.
Figure 4A:
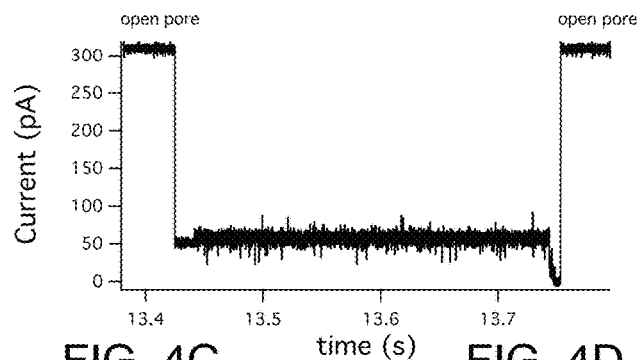
FIGS. 4A-4E show the voltage dependence of the co-translocational unfolding of TrxS112$^{-P}$-oligo(dC)$_{30}$ within the αHL pore.
Figure 4B:
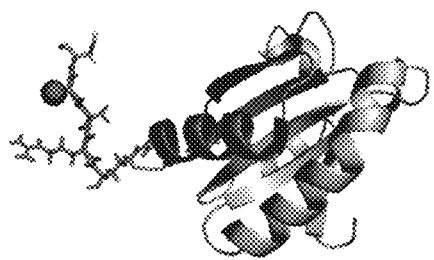
Figure 4C:
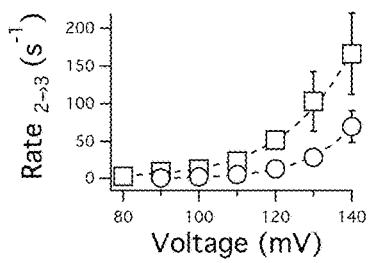
Figure 4D:
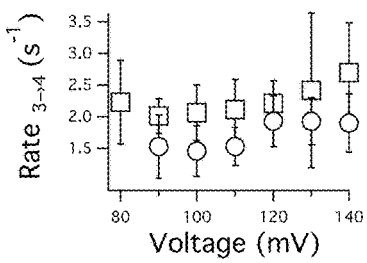
Figure 4E:
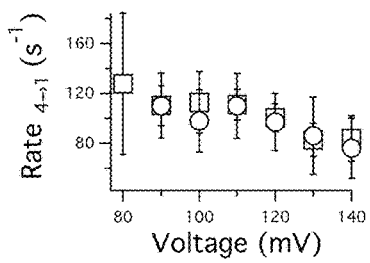
Figure 5A:
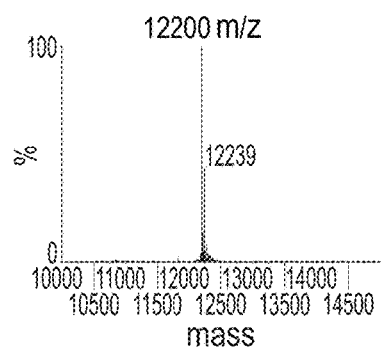
FIGS. 5A-5F show ESI LC-MS in positive ion mode before and after phosphorylation of constructs TrxS112, TrxS107 and TrxS95 (deconvoluted spectra).
Figure 5B:
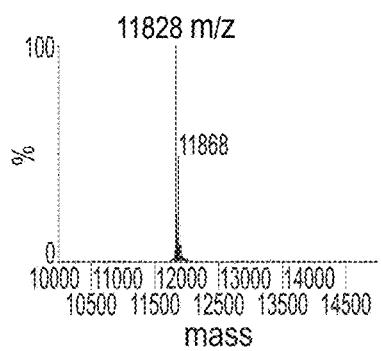
Figure 5C:
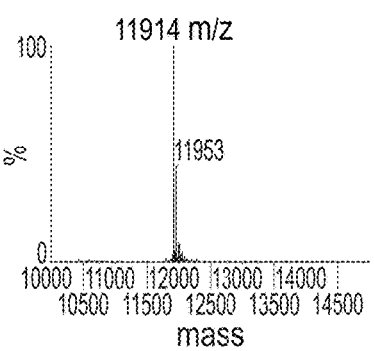
Figure 5D:
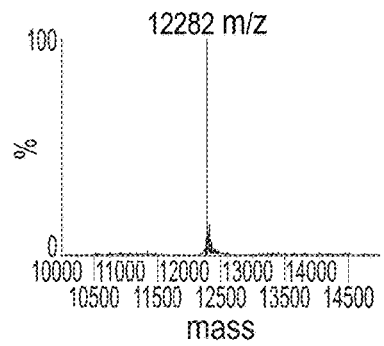
Figure 5E:
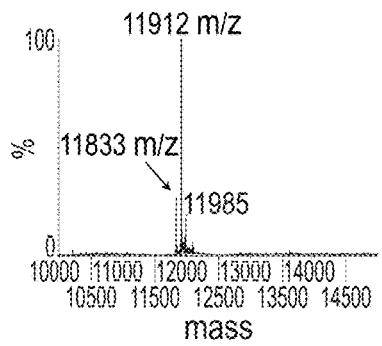
Figure 5F:
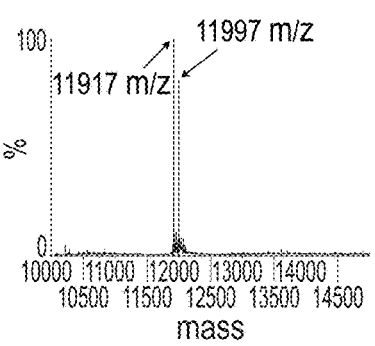
Figure 8A:
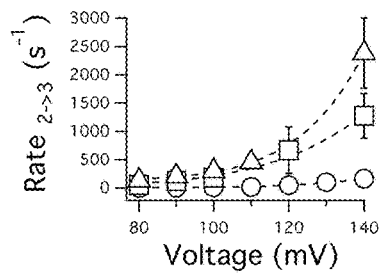
FIGS. 8A-8F show the voltage dependences of the co-translocational unfolding of various Trx within the αHL pore.
Figure 8B:
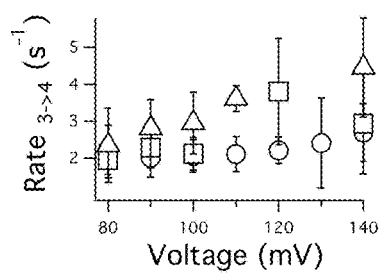
Figure 8C:
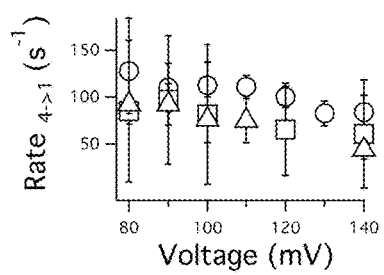
Figure 8D:
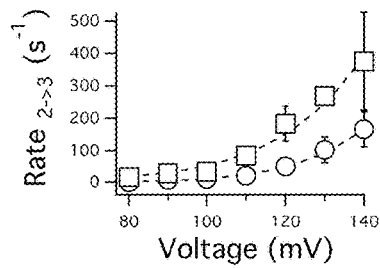
Figure 8E:
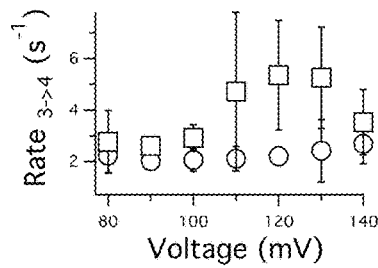
Figure 8F:
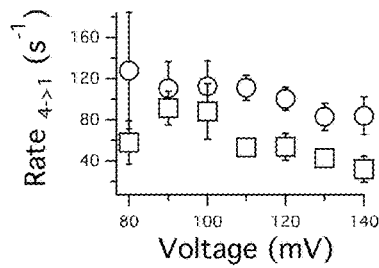

FIGS. 13A-13D show a 2D scatter plot of residual currents ($I_{RES\ \%}$) versus current noise values ($I_n$) for calibration of the pore used in FIG. 3b. (FIG. 13A) The pore was exposed to TrxS107$^{+P}$/A112-oligo(dC)$_{30}$. (FIG. 13B) Without perfusion of the chamber, TrxA107/S112$^{+P}$-oligo(dC)$_{30}$, was then added (two populations are now apparent). (FIG. 13C) TrxS107$^{+P}$/S112$^{+P}$-oligo(dC)$_{30}$ was added to the chamber without prior perfusion. (FIG. 13D) TrxS107$^{-P}$/S112$^{-P}$-oligo(dC)$_{30}$ was added, again without perfusion. The calibration involved a total of 162 events, and was performed with the same pore after data were collected for FIG. 3b. A similar calibration was performed before the experiment, with the phosphorylated Trx added in a different order. A similar result was obtained. Each construct was further analyzed in 3 independent experiments, each with a different pore.

DESCRIPTION OF THE SEQUENCE LISTING

SEQ ID NO: 1 shows the polynucleotide sequence encoding one subunit of wild-type α-hemolysin (WT α-HL).

SEQ ID NO: 2 shows the amino acid sequence of one subunit of WT α-HL.

SEQ ID NO: 3 shows the polynucleotide sequence encoding the LukF subunit of 7-hemolysin.

SEQ ID NO: 4 shows the amino acid sequence of the LukF subunit of 7-hemolysin.

SEQ ID NO: 5 shows the polynucleotide sequence encoding the Hlg2 subunit of 7-hemolysin.

SEQ ID NO: 6 shows the amino acid sequence of the Hlg2 subunit of 7-hemolysin.

SEQ ID NO: 7 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 8 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NOs: 9 to 11 show the amino acid sequences of MspB, C and D.

SEQ ID NOs: 12 to 17 show the proteins used in the Examples.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a pore" includes two or more such pores, reference to "a modification" includes two or more such modifications, reference to "a peptide, polypeptide or protein" includes two or more such peptides, polypeptides or proteins, reference to "an oligonucleotide" includes two or more such oligonucleotides, and the like.

All publications, patents and patent applications cited herein, whether supra or infra, are hereby incorporated by reference in their entirety.

Methods of the Invention

The invention provides a method for determining the presence, absence, number or position(s) of one or more PTMs in a peptide, polypeptide or protein. The invention preferably provides a method for determining the presence, absence, number and position(s) of one or more PTMs in a peptide, polypeptide or protein. The peptide, polypeptide or protein is contacted with a transmembrane pore such that the peptide, polypeptide or protein moves through the pore. One or more current measurements are taken as the peptide, polypeptide or protein moves with respect to the pore. This allows the determination of the presence, absence, number or position(s) of one or more PTMs in the peptide, polypeptide or protein.

The method of the invention allows the rapid detection of PTMs at the single-molecule level through alterations in the current signature through the pore. The method of the invention has several advantages over conventional methods for studying PTMs. It is rapid and simple. It is sensitive because it can identify single PTMs and as well as multiple PTMs. It can also distinguish between adjacent PTMs. The output from the method is analysed in real time, allowing it to be stopped when sufficient information has been obtained. The method can be carried out by someone with minimal training or qualification.

The presence, absence, number or position(s) of any number of PTMs may be determined in accordance with the invention, such as 1 or more, 2 or more, 3 or more, 4 or more, 5 or more, 10 or more, 15 or more, 18 or more PTMs.

The number of PTMs typically depends on the size of the peptide, polypeptide or protein and the number of PTM sites present in the peptide, polypeptide or protein.

Figures 1A, 1B:
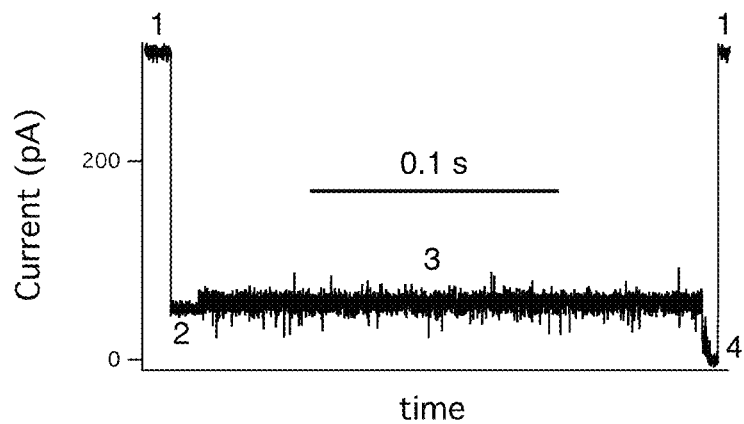

The method of the invention is preferably for determining the presence, absence, number or positions of two or more PTMs in a peptide, polypeptide or protein. In such embodiments, the two or more PTMs may be situated anywhere in the peptide, polypeptide or protein. The two or more PTMs may be at opposite ends of the peptide, polypeptide or protein. The two or more PTMs are preferably separated by 10 or fewer amino acids, 5 or fewer amino acids or 2 or fewer amino acids, such as 1 amino acid. The human genome codifies for 500 kinases, which recognize one or multiple phosphorylation sites. The two or more PTM sites are preferably separated by 10 or fewer amino acids, 5 or fewer amino acids or 2 or fewer amino acids, such as 1 amino acid. PTM sites may comprise two or more amino acids. For instance, possible phosphorylation sites include, but are not limited to, the sequences RRAS and RRNS (FIG. 1b). The serine at the C terminus of these sequences is the amino acid which is modified by phosphorylation. The two or more modified amino acids (i.e. PTM sites) are preferably separated by 10 or fewer amino acids, 5 or fewer amino acids or 2 or fewer amino acids, such as 1 amino acid.

The presence or absence of one or more PTMs can be determined as discussed below. The presence or absence of PTMs, such as phosphorylations, may be used to diagnose diseases as discussed below.

The presence of one or more PTMs indicates that the peptide, polypeptide or protein is post-translationally modified at one or more sites or amino acids. Control experiments can be carried out to determine the current signature(s) associated with the presence of one or more specific PTMs in a specific peptide, polypeptide or protein. Such control signature(s) may then be used to determine the presence of the one or more specific PTMs in accordance with the invention. The presence of the control signature(s) in the method of the invention indicates the presence of the one or more specific PTMs. The absence of the control signature(s) in the method of the invention indicates the absence of the one or more specific PTMs.

Control experiments can also be carried out to determine the current signature(s) associated with the absence of one or more specific PTMs in a specific peptide, polypeptide or protein. Such control signature(s) may then be used to determine the absence of the one or more specific PTMs in accordance with the invention. The presence of the "absence" control signature(s) in the method of the invention indicates the absence of the one or more specific PTMs.

The method of the invention also allows the number and position(s) of one or more specific PTMs to be determined. The position(s) of the PTMs refers to their/its position(s) in the peptide, polypeptide or protein, such as the PTM site or the amino acid which is modified. The positions of two or more PTMs may be determined in accordance with the invention. Control experiments can be carried out to determine the current signatures associated with the presence of different numbers of PTMs at specific positions in a specific peptide, polypeptide or protein. Such control signature(s) may then be used to determine the number and position(s) of the one or more specific PTMs in accordance with the invention. For instance, the presence of a control signature (control signature A for instance) associated with PTMs at specific positions in the method of the invention indicates the presence of the two PTMs at those positions. The presence of a control signature (control signature B for instance) associated with PTMs at specific positions in the method of the invention indicates the presence of one of the two PTMs at a specific position. The absence of a control signature (i.e. the absence of control signatures A and B for instance) in the method of the invention indicates the absence of the two PTMs at those positions.

As indicated above, control experiments can be also carried out to determine the current signatures associated with the absence of different numbers of PTMs at specific positions in a specific peptide, polypeptide or protein. Such control signature(s) may then be used to determine the absence of the relevant number of PTMs at the relevant positions in accordance with the invention.

The method of the invention comprises taking one or more current measurements as the peptide, polypeptide or protein moves with respect to the pore. This can be done as discussed below. The method preferably comprises measuring mean residual current ($I_{RES}$) and/or noise ($I_n$). This can be done as described in the Example. The method more preferably comprises measuring mean residual current ($I_{RES}$) and noise (L). These may then be plotted against each other to given current signatures as described in the Examples.

The method of the invention allows quantification of the different populations of alternative PTMs carried out in the same peptide, polypeptide or protein. This can be done simply counting the number of control signals that carry each PTMs combination. This may allow to relate alterations in the relative populations to a physiological or disease state of the organism.

Peptide, Polypeptide or Protein

The peptide, polypeptide or protein can be naturally-occurring or non-naturally-occurring. The peptide, polypeptide or protein can include within them synthetic or modified amino acids. A number of different types of modification to amino acids are known in the art. Suitable amino acids and modifications thereof are discussed below. For the purposes of the invention, it is to be understood that the peptide, polypeptide or protein can be modified by any method available in the art.

The peptide, polypeptide or protein can be one that is secreted from cells. Alternatively, the peptide, polypeptide or protein can be one that is present inside cells such that it must be extracted from the cells before the invention can be carried out. It can be extracted both by the use of antibodies or by the binding of an affinity tag introduced on the protein.

A peptide is typically a polymer of from about 2 to about 50 amino acids. A polypeptide is typically a longer polymer of amino acids. Proteins are typically polypeptides that are folded into a functional conformation or form part of a functional complex.

Any peptide, polypeptide or protein may be used in the method of the invention. Suitable proteins include, but are not limited to, enzymes, antibodies, hormones, growth factors or growth regulatory proteins, such as cytokines.

The peptide, polypeptide or protein may be bacterial, archaeal, fungal, viral or derived from a parasite. The peptide, polypeptide or protein may derived from a plant. The peptide, polypeptide or protein is preferably mammalian, more preferably human.

Contacting and Translocation

Steps (a) and (b) in the method of the invention are preferably carried out with a potential applied across the pore. The applied potential typically causes the peptide, polypeptide or protein to translocate or move through the pore. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5.

Folded peptides, polypeptides or proteins can be translocated through a pore as described in Rodriguez-Larrea, D. & Bayley, H. Multistep protein unfolding during nanopore translocation. *Nat. Nanotechnol.* 8 288-95 (2013). In particular, the peptide, polypeptide or protein is preferably covalently attached to a charged polymer, such as an oligonucleotide. Alternatively, the peptide, polypeptide or protein can carry a leader sequence that drives it to the pore. Also, molecular motors can be used to pull the peptide, polypeptide or protein through the pore as in Nivala, J., Marks, D. B., Akeson M. Unfoldase-mediated protein translocation through an α-hemolysin nanopore. *Nat. Biotech.* 31 247-50 (2013). More preferably, the amino- (N-) or carboxy- (C-) terminus of the peptide, polypeptide or protein is covalently attached to a charged polymer, such as an oligonucleotide. The peptide, polypeptide or protein may be covalently attached to the charged polymer, such as an olignucleotide, using any of the methods discussed below. The peptide, polypeptide or protein may be covalently attached to the charged polymer, such as an olignucleotide, using a linker. Suitable linkers are known in the art.

The charged polymer, such as an oligonucleotide, is translocated through the pore under the influence of the applied potential. This typically has three effects: (1) it facilitates the threading of the N- or C-terminus of the peptide, polypeptide or protein into the pore; (2) it provides a tunable driving force both for peptide, polypeptide or protein unfolding and the early stages of peptide, polypeptide or protein translocation; and (3) it prevents backward movement of the peptide, polypeptide or protein.

Any oligonucleotide may be used. Oligonucleotides are short nucleotide polymers which typically have 50 or fewer nucleotides, such 40 or fewer, 30 or fewer, 20 or fewer, 10 or fewer or 5 or fewer nucleotides. The oligonucleotide is typically single stranded.

A nucleotide typically contains a nucleobase, a sugar and at least one phosphate group. The nucleobase is typically heterocyclic. Nucleobases include, but are not limited to, purines and pyrimidines and more specifically adenine (A), guanine (G), thymine (T), uracil (U) and cytosine (C). The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate, cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP), 5-methyl-2'-deoxycytidine monophosphate, 5-methyl-2'-deoxycytidine diphosphate, 5-methyl-2'-deoxycytidine triphosphate, 5-hydroxymethyl-2'-deoxycytidine monophosphate, 5-hydroxymethyl-2'-deoxycytidine diphosphate and 5-hydroxymethyl-2'-deoxycytidine triphosphate. The nucleotides are preferably selected from AMP, TMP, GMP, UMP, dAMP, dTMP, dGMP or dCMP. The nucleotides may be abasic (i.e. lack a nucleobase). The nucleotides may contain additional modifications. In particular, suitable modified nucleotides include, but are not limited to, 2'amino pyrimidines (such as 2'-amino cytidine and 2'-amino uridine), 2'-hydroxyl purines (such as, 2'-fluoro pyrimidines (such as 2'-fluorocytidine and 2'fluoro uridine), hydroxyl pyrimidines (such as 5'-α-P-borano uridine), 2'-O-methyl nucleotides (such as 2'-O-methyl adenosine, 2'-O-methyl guanosine, 2'-O-methyl cytidine and 2'-O-methyl uridine), 4'-thio pyrimidines (such as 4'-thio uridine and 4'-thio cytidine) and nucleotides have modifications of the nucleobase (such as 5-pentynyl-2'-deoxy uridine, 5-(3-aminopropyl)-uridine and 1,6-diaminohexyl-N-5-carbamoylmethyl uridine).

A nucleotide may be abasic (i.e. lack a nucleobase). A nucleotide may also lack a nucleobase and a sugar (i.e. is a C3 spacer).

PTMs

Any one or more PTMs may be determined in accordance with the invention. The one or more PTMs are preferably selected from modification with a hydrophobic group, modification with a cofactor, addition of a chemical group, glycation (the non-enzymatic attachment of a sugar), biotinylation and pegylation. PTMs can also be non-natural, such that they are chemical modifications done in the laboratory for biotechnological or biomedical purposes. This can allow monitoring the levels of the laboratory made peptide, polypeptide or protein in contrast to the natural counterparts.

The modification with a hydrophobic group is preferably selected from myristoylation, attachment of myristate, a C14 saturated acid; palmitoylation, attachment of palmitate, a C16 saturated acid; isoprenylation or prenylation, the attachment of an isoprenoid group; farnesylation, the attachment of a farnesol group; geranylgeranylation, the attachment of a geranylgeraniol group; and glypiation, glycosylphosphatidylinositol (GPI) anchor formation via an amide bond.

The modification with a cofactor is preferably selected from lipoylation, attachment of a lipoate (C8) functional group; flavination, attachment of a flavin moiety (e.g. flavin mononucleotide (FMN) or flavin adenine dinucleotide (FAD)); attachment of heme C, for instance via a thioether bond with cysteine; phosphopantetheinylation, the attachment of a 4'-phosphopantetheinyl group; and retinylidene Schiff base formation.

The addition of a chemical group is preferably selected from acylation, e.g. O-acylation (esters), N-acylation (amides) or S-acylation (thioesters); acetylation, the attachment of an acetyl group for instance to the N-terminus or to lysine; formylation; alkylation, the addition of an alkyl group, such as methyl or ethyl; methylation, the addition of a methyl group for instance to lysine or arginine; amidation; butyrylation; gamma-carboxylation; glycosylation, the enzymatic attachment of a glycosyl group for instance to arginine, asparagine, cysteine, hydroxylysine, serine, threonine, tyrosine or tryptophan; polysialylation, the attachment of polysialic acid; malonylation; hydroxylation; iodination; bromination; citrulination; nucleotide addition, the attachment of any nucleotide such as any of those discussed above, ADP ribosylation; oxidation; phosphorylation, the attachment of a phosphate group for instance to serine, threonine or tyrosine (O-linked) or histidine (N-linked); adenylylation, the attachment of an adenylyl moiety for instance to tyrosine (O-linked) or to histidine or lysine (N-linked); propionylation; pyroglutamate formation; S-glutathionylation; Sumoylation; S-nitrosylation; succinylation, the attachment of a succinyl group for instance to lysine; selenoylation, the incorporation of selenium; and ubiquitinilation, the addition of ubiquitin subunits (N-linked).

The addition of a chemical group may concern any non-natural chemical modification of one or more cysteines, lysines, tyrosines, arginines or any other (natural or not) residue within the peptide, polypeptide or protein.

The method of the invention is preferably for determining the presence, absence, number or position(s) of one or more phosphorylations or two or more two or more phosphorylations. Any phosphorylations may be determined, including phosphorylation of serine, threonine or tyrosine (O-linked) or phosphorylation of histidine (N-linked). The one or more phosphorylations are preferably O-linked. The one or more phosphorylations are more preferably one or more phosphorylations of serine.

Transmembrane Pore

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well in the membrane along which or into which hydrated ions may flow. The transmembrane protein pore allows the peptide, polypeptide or protein to be moved through the pore and typically cross the membrane.

Any membrane may be used in accordance with the invention. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer.

The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Examples. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and $SiO$, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647). In another preferred embodiment an amphiphilic layer may be formed across or on top of a solid state pore. This may be described in the art as hybrid pore formation (Hall et al., Nat Nanotechnol., 2010, 5, 874-877). The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below. The method of the invention is typically carried out in vitro.

The peptide, polypeptide or protein is preferably coupled to the membrane, for example as described in PCT/GB12/051191. This may be done using any known method. If the membrane is an amphiphilic layer, such as a lipid bilayer (as discussed in detail above), the peptide, polypeptide or protein is preferably coupled to the membrane via a polypeptide present in the membrane or a hydrophobic anchor present in the membrane. The hydrophobic anchor is preferably a lipid, fatty acid, sterol, carbon nanotube or amino acid.

The peptide, polypeptide or protein may be coupled directly to the membrane. The peptide, polypeptide or protein is preferably coupled to the membrane via a linker. Preferred linkers include, but are not limited to, polymers, such as polynucleotides, polyethylene glycols (PEGs) and polypeptides.

The coupling may be stable or transient. For certain applications, the transient nature of the coupling is preferred. Transient coupling minimises permanent blocking allowing data to be accumulated more quickly as time is not lost in manually unblocking the pore. When permanent coupling is used the amphiphilic layer may be destabilized or it could cause the build up of tethered peptides, polypeptides or proteins on the cis side, thus altering the experimental equilibrium. These effects can be minimised by coupling transiently. Chemical groups that form stable or transient links with the membrane are discussed in more detail below. The peptide, polypeptide or protein may be transiently coupled to an amphiphilic layer, such as a lipid bilayer using cholesterol or a fatty acyl chain. Any fatty acyl chain having a length of from about 6 to about 30 carbon atoms, such as hexadecanoic acid, may be used.

Coupling to synthetic lipid bilayers has been carried out previously with various different tethering strategies. These are summarised in Table 1 below.

TABLE 1

| Attachment group | Type of coupling | Reference |
| --- | --- | --- |
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholesterol | Transient | Pfeiffer, I. and F. Hook (2004). "Bivalent cholesterol-based coupling of oligonucletides to lipid membrane assemblies." *J Am Chem Soc* 126(33): 10224-5 |
| Lipid | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

The transmembrane pore is preferably a transmembrane protein pore. A transmembrane protein pore is a polypeptide or a collection of polypeptides that permits hydrated ions to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analytes, such as nucleotides, to flow from one side of the membrane, such as a lipid bilayer, to the other. The transmembrane protein pore allows the peptide, polypeptide or protein to be moved through the pore.

The barrel or channel of the pore (through which hydrated ions flow) may have any width as long as the peptide, polypeptide or protein can move through the pore. The barrel or channel typically has more than one width, i.e. the width of the barrel or channel may change along its length. The pore has a narrowest part, known in the art as the constriction site. This is the narrowest part of the barrel or channel. The location of the narrowest part can be determined using any method known in the art. The narrowest part of a protein pore may be identified using protein modelling, x-ray diffraction measurement of the protein in a crystalline state (Rupp B (2009). Biomolecular Crystallography: Principles, Practice and Application to Structural Biology. New York: Garland Science.), nuclear magnetic resonance (NMR) spectroscopy of the protein in solution (Mark Rance; Cavanagh, John; Wayne J. Fairbrother; Arthur W. Hunt III; Skelton, Nicholas J. (2007). Protein NMR spectroscopy: principles and practice (2nd ed.). Boston: Academic Press.) or cryo-electron microscopy of the protein in a frozen-hydrated state (van Heel M, Gowen B, Matadeen R, Orlova E V, Finn R, Pape T, Cohen D, Stark H, Schmidt R, Schatz M, Patwardhan A (2000). "Single-particle electron cryo-microscopy: towards atomic resolution". Q Rev Biophys. 33: 307-69. Structural information of proteins determined by above mentioned methods are publicly available from the protein bank (PDB) database.

Protein modelling exploits the fact that protein structures are more conserved than protein sequences amongst homologues. Hence, producing atomic resolution models of proteins is dependent upon the identification of one or more protein structures that are likely to resemble the structure of the query sequence. In order to assess whether a suitable protein structure exists to use as a "template" to build a protein model, a search is performed on the protein data bank (PDB) database. A protein structure is considered a suitable template if it shares a reasonable level of sequence identity with the query sequence. If such a template exists, then the template sequence is "aligned" with the query sequence, i.e. residues in the query sequence are mapped onto the template residues. The sequence alignment and template structure are then used to produce a structural model of the query sequence. Hence, the quality of a protein model is dependent upon the quality of the sequence alignment and the template structure.

The narrowest part of the pore is sufficiently wide to permit the peptide, polypeptide or protein, and the charged polymer if present, to enter it and translocate it.

The transmembrane protein pore may be a monomer or an oligomer. The pore is preferably made up of several repeating subunits, such as 6, 7, 8 or 9 subunits. The pore is preferably a hexameric, heptameric, octameric or nonameric pore.

The transmembrane protein pore typically comprises a barrel or channel through which ions may flow. The subunits of the pore typically surround a central axis and contribute strands to a transmembrane β barrel or channel or a transmembrane α-helix bundle or channel. The barrel or channel of the transmembrane protein pore typically comprises amino acids that facilitate interaction with the one or more PTMs. These amino acids are preferably located at or near the narrowest part of the pore, such as at or near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and negatively-charged phosphate groups.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB or MspC, outer membrane phospholipase A, *Neisseria* autotransporter lipoprotein (NalP) or a pore from the Omp family (e.g. Omp F, OmpG etc.). α-helix bundle pores comprise a barrel or channel that is formed from α-helices. Suitable α-helix bundle pores include, but are not limited to, inner membrane proteins and α outer membrane proteins, such as Wza and ClyA toxin. The transmembrane pore is preferably derived from α-hemolysin (α-HL), from leukocidin or from MspA.

The pore may be a homo-oligomer (all monomer units identical) or a hetero-oligomer (two or more different types of monomer). The pore may comprise linked monomers, for example dimers that assemble into the oligomeric structure of the pore. The monomers may be connected in the same polypeptide strand, i.e. genetically fused.

The pore may comprise at least one dimer and 1, 2, 3, 4, 5, 6, 7 or 8 monomers. The pore may comprise two, three, four or more dimers. Such pores further comprise sufficient monomers to form the pore. A further pore comprises only dimers, for example a pore may comprise 4, 5, 6, 7 or 8 dimers. A specific pore for use according to the inventions comprises four dimers. The dimers may oligomerise into a pore with a structure such that only one monomer of a dimer contributes to the barrel or vestibule of the pore. Typically the other monomers of the construct will be on the outside of the barrel or vestibule of the pore. For example, a pore may comprise 5, 6, 7 or 8 dimers where the barrel or vestibule comprises 8 monomers.

The transmembrane protein pore is preferably derived from α-hemolysin (α-HL). The wild type α-HL pore is formed of seven identical monomers or subunits (i.e. it is heptameric). The transmembrane protein pore preferably comprises seven monomers derived from α-HL. The sequence of one wild-type monomer or subunit of α-hemolysin (WT α-HL) is shown in SEQ ID NO: 2. The transmembrane protein pore preferably comprises seven monomers each comprising the sequence shown in SEQ ID NO: 2 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 2 form part of a constriction of the barrel or channel of α-HL.

The pore preferably comprises seven proteins or monomers each comprising the sequence shown in SEQ ID NO: 2 or a variant thereof. The transmembrane protein is preferably (a) formed of seven identical subunits as shown in SEQ ID NO: 2 or (b) a variant thereof in which one or more of, or all of, the seven subunits is a variant of SEQ ID NO: 2 and which retains pore activity. 1, 2, 3, 4, 5, 6 or 7 of the subunits may be variants. The variants in a pore may be the same or different. The seven subunits may be the same (homoheptamer) or different (heteroheptamer).

A variant of SEQ ID NO: 2 is a protein that has an amino acid sequence which varies from that of SEQ ID NO: 2 and which retains its pore forming ability. The ability of a variant to form a pore can be assayed using any method known in the art. For instance, the variant may be inserted into an amphiphilic layer, such as a lipid bilayer, along with other appropriate subunits and its ability to oligomerise to form a pore may be determined. Methods are known in the art for inserting subunits into amphiphilic layers, such as lipid bilayers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

One preferred variant of SEQ ID NO: 2 is α-hemolysin-NN which contains the substitutions E111N and K147N (Stoddart et al., PNAS, 2009; 106(19): 7702-7707).

The variant may include modifications that facilitate covalent attachment to or interaction with another molecule. The variant preferably comprises one or more reactive cysteine residues that facilitate attachment. For instance, the variant may include a cysteine at one or more of positions 8, 9, 17, 18, 19, 44, 45, 50, 51, 237, 239 and 287 and/or on the amino or carboxy terminus of SEQ ID NO: 2. Preferred variants comprise a substitution of the residue at position 8, 9, 17, 237, 239 and 287 of SEQ ID NO: 2 with cysteine (A8C, T9C, N17C, K237C, S239C or E287C). The variant is preferably any one of the variants described in International Application No. PCT/GB09/001690 (published as WO 2010/004273), PCT/GB09/001679 (published as WO 2010/004265) or PCT/GB10/000133 (published as WO 2010/086603).

The variant may be a naturally occurring variant which is expressed naturally by an organism, for instance by a *Staphylococcus* bacterium. Alternatively, the variant may be expressed in vitro or recombinantly by a bacterium such as *Escherichia coli*. Variants also include non-naturally occurring variants produced by recombinant technology. The variant may include non-naturally occurring amino acids or other molecules that can be introduced by native or non-native chemical ligation. The variant may also include non-covalent modifications such as the use of cyclodextrin as adapters; these modifications include molecules that bind tightly to the pore.

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 200 or more, for example 230, 250, 270 or 280 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/).

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume.

The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 2 below. Where amino acids have similar polarity, this can also be determined by reference to the hydropathy scale for amino acid side chains in Table 3. Non-conservative replacements can be made too while the protein pore retains its structure and function.

TABLE 2

Chemical properties of amino acids

| | |
|---|---|
| Ala | aliphatic, hydrophobic, neutral |
| Cys | polar, hydrophobic, neutral |
| Asp | polar, hydrophilic, charged (−) |
| Glu | polar, hydrophilic, charged (−) |
| Phe | aromatic, hydrophobic, neutral |
| Gly | aliphatic, neutral |
| His | aromatic, polar, hydrophilic, charged (+) |
| Ile | aliphatic, hydrophobic, neutral |
| Lys | polar, hydrophilic, charged(+) |
| Leu | aliphatic, hydrophobic, neutral |
| Met | hydrophobic, neutral |
| Asn | polar, hydrophilic, neutral |
| Pro | hydrophobic, neutral |
| Gln | polar, hydrophilic, neutral |
| Arg | polar, hydrophilic, charged (+) |
| Ser | polar, hydrophilic, neutral |
| Thr | polar, hydrophilic, neutral |
| Val | aliphatic, hydrophobic, neutral |
| Trp | aromatic, hydrophobic, neutral |
| Tyr | aromatic, polar, hydrophobic |

TABLE 3

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 200 or 250 amino acids in length. Such fragments may be used to produce the pores. A fragment preferably contains the pore forming domain of SEQ ID NO: 2. Fragments typically include residues 119, 121, 135, 113 and 139 of SEQ ID NO: 2.

One or more amino acids may be alternatively (insertions) or additionally added to the polypeptides described above. An extension may be provided at the amino terminal or carboxy terminal of the amino acid sequence of SEQ ID NO: 2 or polypeptide variant or fragment thereof. The extension may be quite short, for example from about 1 to about 10 amino acids in length. Alternatively, the extension may be longer, for example up to about 50 or about 100 amino acids.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of α-HL, which contains a β-barrel, is provided by β-strands in each subunit. This segments can be shortened making the β-barrel shorter but still retaining the ability to form a pore in the membrane. A variant of SEQ ID NO: 2 typically comprises the regions in SEQ ID NO: 2 that form β-strands. The amino acids of SEQ ID NO: 2 that form β-strands are discussed above. One or more modifications can be made to the regions of SEQ ID NO: 2 that form β-strands as long as the resulting variant retains its ability to form a pore. Specific modifications that can be made to the β-strand regions of SEQ ID NO: 2 are discussed above.

A variant of SEQ ID NO: 2 preferably includes one or more modifications, such as substitutions, additions or deletions, within its α-helices, β 3 strands and/or loop regions. Amino acids that form α-helices and loops are discussed above.

The transmembrane protein pore is also preferably derived from leukocidin. A leukocidin is a hetero-oligomeric pore with two different subunits, one class S subunit and one class F subunit. Suitable leukocidins include, but are not limited to, gamma hemolysin (γ-HL) comprising LukF (HlgB) and Hlg2 (HlgA), leukocidin comprising LukF (HlgB) and LukS (HlgC), leukocidin PV comprising LukF-PV and LukS-PV, LukE/LukD pore comprising LukE and LukD and LukS-I/LukF-I comprising LukF-I and LukS-I.

When the transmembrane protein pore is a leukocidin, it is preferably derived from gamma hemolysin (γ-HL). The wild type γ-HL pore is formed of eight subunits (i.e. it is octameric) and contains four subunits of LukF and four subunits of Hlg2. The sequence of one monomer or subunit of LukF is shown in SEQ ID NO: 4. The sequence of one monomer or subunit of Hlg2 is shown in SEQ ID NO: 6. The transmembrane protein pore preferably comprises four monomers each comprising the sequence shown in SEQ ID NO: 4 or a variant thereof and four monomers each comprising the sequence shown in SEQ ID NO: 6 or a variant thereof. Amino acids 109-147 of SEQ ID NO: 4 and 103-139 of SEQ ID NO: 6 form loop regions.

The γ-hemolysin pore is preferably (a) γ-hemolysin formed of four identical subunits as shown in SEQ ID NO: 4 and four identical subunits as shown in SEQ ID NO: 6 or (b) a variant thereof in which one or more of, or all of, the subunits is a variant of SEQ ID NO: 4 and/or one or more of, or all of, the subunits is a variant of SEQ ID NO: 6 and the pore retains pore activity. Such pores are hetero-octamers. 1, 2, 3 or 4 of the subunits may be variants of SEQ ID NO: 4 and/or 6. The variants in a pore may be the same or different.

A variant of SEQ ID NO: 4 or 6 is a protein that has an amino acid sequence which varies from that of SEQ ID NO: 4 or 6 and which retains its pore forming ability. The ability of a variant to form a pore can be assayed using any method known in the art. For instance, the variant may be inserted into an amphiphilic layer, such as a lipid bilayer, along with other appropriate subunits and its ability to oligomerise to form a pore may be determined. Methods are known in the art for inserting subunits into amphiphilic layers, such as lipid bilayers. Suitable methods are discussed above.

The variant may include modifications that facilitate covalent attachment to or interaction with another molecule. The variant preferably comprises one or more reactive cysteine residues that facilitate attachment. The variant may also include non-covalent modifications such as the use of cyclodextrin as adapters; these modifications include molecules that bind tightly to the pore.

The variant may be a naturally occurring variant which is expressed naturally by an organism, for instance by a *Staphylococcus* bacterium. Alternatively, the variant may be expressed in vitro or recombinantly by a bacterium such as *Escherichia coli*. Variants also include non-naturally occurring variants produced by recombinant technology. Over the entire length of the amino acid sequence of SEQ ID NO: 4 or 6, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 or 6 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 or 6 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 or 6 may additionally be deleted from the polypeptides described above. Up to 1, 2, 3, 4, 5, 10, 20 or 30 residues may be deleted, or more.

Variants may be fragments of SEQ ID NO: 4 or 6. Such fragments retain pore-forming activity. Fragments may be at least 50, 100, 200 or 250 amino acids in length. A fragment preferably comprises the pore-forming domain of SEQ ID NO: 4 or 6.

One or more amino acids may be alternatively (insertions) or additionally added to the polypeptides described above. An extension may be provided at the amino terminus or carboxy terminus of the amino acid sequence of SEQ ID NO: 4 or 6 or a variant or fragment thereof. The extension may be quite short, for example from about 1 to about 10 amino acids in length. Alternatively, the extension may be longer, for example up to about 50 or about 100 amino acids. A carrier protein may be fused to a pore or variant.

As discussed above, a variant of SEQ ID NO: 4 or 6 is a subunit that has an amino acid sequence which varies from that of SEQ ID NO: 4 or 6 and which retains its ability to form a pore. A variant typically contains the regions of SEQ ID NO: 4 or 6 that are responsible for pore formation. The pore forming ability of γ-HL, which contains a β-barrel, is provided by β-strands in each subunit. A variant of SEQ ID NO: 4 or 6 typically comprises the regions in SEQ ID NO: 4 or 6 that form β-strands. The amino acids of SEQ ID NO: 4 or 6 that form β-strands are discussed above. One or more modifications can be made to the regions of SEQ ID NO: 4 or 6 that form β-strands as long as the resulting variant retains its ability to form a pore. Specific modifications that can be made to the β-strand regions of SEQ ID NO: 4 or 6 are discussed above.

A variant of SEQ ID NO: 4 or 6 preferably includes one or more modifications, such as substitutions, additions, insertions or deletions, within its α-helices and/or loop regions. Amino acids that form α-helices and loops are discussed above.

The transmembrane protein pore is preferably derived from Msp, preferably from MspA.

Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 8 or a variant thereof. SEQ ID NO: 8 is the MS-(B1)8 mutant of the MspA monomer. It includes the following mutations: D90N, D91N, D93N, D118R, D134R and E139K. A variant of SEQ ID NO: 8 is a polypeptide that has an amino acid sequence which varies from that of SEQ ID NO: 8 and which retains its ability to form a pore. The ability of a variant to form a pore can be assayed using any method known in the art as discussed above.

Over the entire length of the amino acid sequence of SEQ ID NO: 8, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 8 over the entire sequence. There may be at least 80%, for example at least 85%, 90% or 95%, amino acid identity over a stretch of 100 or more, for example 125, 150, 175 or 200 or more, contiguous amino acids ("hard homology"). Standard methods in the art may be used to determine homology as discussed above.

SEQ ID NO: 8 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 8 has the mutation L88N in addition to all the mutations of MS-B1 and is called MS-(B2)8. The pore used in the invention is preferably MS-(B2)8. A variant of SEQ ID NO: 8 has the mutations G75S/G77S/L88N/Q126R in addition to all the mutations of MS-B1 and is called MS-B2C. The pore used in the invention is preferably MS-(B2)8 or MS-(B2C)8.

Amino acid substitutions may be made to the amino acid sequence of SEQ ID NO: 8 in addition to those discussed above, for example up to 1, 2, 3, 4, 5, 10, 20 or 30 substitutions. The substitutions may be conservative as discussed above and shown in Tables 2 and 3.

One or more amino acid residues of the amino acid sequence of SEQ ID NO: 8 may additionally be deleted from the polypeptides described above. Up to 1, 2, 3, 4, 5, 10, 20 or 30 residues may be deleted, or more.

Variants may include fragments of SEQ ID NO: 8. Such fragments retain pore forming activity. Fragments may be at least 50, 100, 150 or 200 amino acids in length. Such fragments may be used to produce the pores. A fragment preferably comprises the pore forming domain of SEQ ID NO: 8. Fragments must include one of residues 88, 90, 91, 105, 118 and 134 of SEQ ID NO: 8. Typically, fragments include all of residues 88, 90, 91, 105, 118 and 134 of SEQ ID NO: 8.

One or more amino acids may be alternatively or additionally added to the polypeptides described above. An extension may be provided at the amino terminal or carboxy terminal of the amino acid sequence of SEQ ID NO: 8 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 8 and which retains its ability to form a pore. A variant typically contains the regions of SEQ ID NO: 8 that are responsible for pore formation. The pore forming ability of Msp, which contains a β-barrel, is provided by β-sheets in each subunit. A variant of SEQ ID NO: 8 typically comprises the regions in SEQ ID NO: 8 that form β-sheets. One or more modifications can be made to the regions of SEQ ID NO: 8 that form β-sheets as long as the resulting variant retains its ability to form a pore. A variant of SEQ ID NO: 8 preferably includes one or more modifications, such as substitutions, additions or deletions, within its α-helices and/or loop regions.

In some embodiments, the transmembrane protein pore is chemically modified. The monomers derived from α-HL (i.e. SEQ ID NO: 2 or a variant thereof), γ-HL (i.e. SEQ ID NO: 4 or 6 or a variant thereof) or MspA (SEQ ID NO: 8 or a variant thereof) may be modified to assist their identification or purification, for example by the addition of histidine residues (a Histag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating α-HL hetero-oligomers (Chem Biol. 1997 July; 4(7):497-505).

The monomer derived from α-HL, γ-HL or MspA may be labelled with a revealing label. The revealing label may be any suitable label which allows the pore to be detected. Suitable labels include, but are not limited to, fluorescent molecules, radioisotopes, e.g. $^{125}I$, $^{35}S$, enzymes, antibodies, antigens, polynucleotides and ligands such as biotin.

The monomer derived from α-HL, γ-HL or MspA may also be produced using D-amino acids. For instance, the monomer derived from α-HL, γ-HL or MspA may comprise a mixture of L-amino acids and D-amino acids. This is conventional in the art for producing such proteins or peptides.

The monomer derived from α-HL, γ-HL or MspA may contain one or more specific modifications to facilitate interactions with the peptide, polypeptide or protein. The monomer derived from α-HL or γ-HL may also contain other non-specific modifications as long as they do not interfere with pore formation. A number of non-specific side chain modifications are known in the art and may be made to the side chains of the monomer derived from α-HL, γ-HL or MspA. Such modifications include, for example, reductive alkylation of amino acids by reaction with an aldehyde followed by reduction with $NaBH_4$, amidination with methylacetimidate or acylation with acetic anhydride. Such modifications also include the modification of one or more cysteine residues present in the sequence by sulfhydryl chemistry.

The monomer derived from α-HL, γ-HL or MspA can be produced using standard methods known in the art. The monomer may be made synthetically or by recombinant means. For example, the pore may be synthesized by in vitro translation and transcription (IVTT) or by native chemical ligation. Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

The pore can be produced using standard methods known in the art. Polynucleotide sequences encoding a pore may be derived and replicated using standard methods in the art. Polynucleotide sequences encoding a pore may be expressed in a bacterial host cell using standard techniques in the art. The pore may be produced in a cell by in situ expression of the polypeptide from a recombinant expression vector. The expression vector optionally carries an inducible promoter to control the expression of the polypeptide. These methods are described in described in Sambrook, J. and Russell, D. (2001). Molecular Cloning: A Laboratory Manual, 3rd Edition. Cold Spring Harbor Laboratory Press, Cold Spring Harbor, N.Y. The pore may also be produced by in vitro transcription and translation and purified in small scale by SDS-PAGE.

The pore may be produced in large scale following purification by any protein liquid chromatography system from protein producing organisms or after recombinant expression. Typical protein liquid chromatography systems include size-exclusion chromatography, affinity purification, FPLC, AKTA systems, the Bio-Cad system, the Bio-Rad BioLogic system and the Gilson HPLC system.

Apparatus and Conditions

Electrical measurements may be made using standard single channel recording equipment as describe in Stoddart, D. S., et al., (2009), *Proceedings of the National Academy of Sciences of the United States of America* 106, p7702-7707, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

The methods may be carried out using any apparatus that is suitable for investigating a membrane/pore system in which a pore is inserted into a membrane. The method may be carried out using any apparatus that is suitable for transmembrane pore sensing. For example, the apparatus comprises a chamber comprising an aqueous solution and a barrier that separates the chamber into two sections. The barrier has an aperture in which the membrane containing the pore is formed. The methods may also be carried out using droplet interface bilayers (DIBs). Two water droplets are placed on the electrodes and immersed into a oil/phospholipid mixture. The two droplets are taken in close contact and at the interface a phospholipid membrane is formed where the pores get inserted.

The methods may be carried out using the apparatus described in International Application No. PCT/GB08/000562 (WO 2008/102120).

The methods involve measuring the current flowing through the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods may be carried out on a silicon-based array of wells where each array comprises 128, 256, 512, 1024 or more wells.

The methods of the invention may involve the measuring of a current flowing through the pore. Suitable conditions for measuring ionic currents through transmembrane pores are known in the art and disclosed in the Example. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different PTMs by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. The salt concentration can be different at both sides of the membrane, such as 0.1 M at one side and 3 M at the other. The salt and composition used on each side of the membrane may be also different. High salt concentrations provide a high signal to noise ratio and allow for currents indicative PTMs to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

The peptide, polypeptide or protein may be contacted with the pore on either side of the membrane.

Diagnostic Method

The invention also provides a method of determining whether or not an organism has a disease, disorder or phenotype associated with one or more PTMs of a peptide, polypeptide or protein. The one or more PTMs may be normal or abnormal. The invention preferably provides a method of determining whether or not an organism has a disease, disorder or phenotype associated with abnormal phosphorylation of a peptide, polypeptide or protein.

The organism is typically one who is suspected of having the disease, disorder or phenotype. For example, an organism who is suspected of having the disease or disorder may exhibit symptoms of the disease or disorder. In other words, the organism may be symptomatic. The organism may be genetically predisposed to the disease or disorder. However, the organism may not necessarily exhibit any symptoms of the disease or disorder. In other words, the organism may be asymptomatic.

Typically, the organism is human, but alternatively it may be another mammal such as a commercially farmed animal, such as a horse, a cow, a sheep or a pig, or may alternatively be a pet, such as a cat, a dog or a rodent (especially a rat or a mouse), or an experimental animal. The organism is typically an individual or a patient. Alternatively, the organism may be a plant, a fungus or any unicellular organism.

A disease, disorder or phenotype is associated with one or more PTMs of a peptide, polypeptide or protein if an organism having the disease, disorder or phenotype exhibits a peptide, polypeptide or protein having the one or more PTMs. A disease, disorder or phenotype is associated with one or more abnormal PTMs of a peptide, polypeptide or protein if an organism having the disease or disorder exhibits a peptide, polypeptide or protein whose one or more PTMs differs from that of the peptide, polypeptide or protein observed in normal organisms, i.e. whose one or more PTMs differ from normal PTM(s) of the peptide, polypeptide or protein. An abnormal PTM of the peptide, polypeptide or protein may be the presence of one or more PTMs which are normally absent, the absence of one or more PTMs which are normally present, an increased number of PTMs, a decreased number of PTMs, a change in the PTM pattern or a combination thereof.

A disease or disorder is associated with abnormal phosphorylation if an organism having the disease or disorder exhibits a peptide, polypeptide or protein whose phosphorylation differs from the phosphorylation of the peptide, polypeptide or protein observed in normal organisms, i.e. whose phosphorylation differs from normal phosphorylation of the peptide, polypeptide or protein. An abnormal phosphorylation of the peptide, polypeptide or protein may be the presence of one or more phosphorylations which are normally absent, the absence of one or more phosphorylations which are normally present, an increased number of phosphorylations, a decreased number of phosphorylations, a change in the phosphorylation pattern or a combination thereof.

Diseases associated with abnormal phosphorylation of a peptide, polypeptide or protein are well known in the art[45]. Diseases or disorders that may be diagnosed in accordance with the invention include, but are not limited to, cancer, chronic inflammatory disease, myotonic muscular dystrophy, X-Linked agammaglobulinaemia, Bruton tyrosine kinase, hirschsprungís disease, autosomal recessive SCID, X-Linked SCID, chraniosynostosis, papillary renal cancer, chronic myelomonocytic leukaemia, chronic myelogenous leukaemia, non-Hodgkins lymphoma, Peutz-Jeghers syndrome, Coffin-Lowry syndrome, ataxia-telangiectasia, Li-Fraumeni syndrome, Williams syndrome, Leprechaunism, diabetes, Wolff-Parkinson-White syndrome, Wolcott-Rallison syndrome or X-Linked myotubular myopathy.

In each instance, the skilled person will understand which peptide, polypeptide or protein to investigate using the method of the invention. An abnormal phosphorylation of the peptide, polypeptide or protein indicates that the organism has the relevant disease or disorder. A normal phosphorylation of the peptide, polypeptide or protein indicates that the organism does not have the relevant disease or disorder.

The method comprises carrying out the method of the invention on a sample from the organism comprising the peptide, polypeptide or protein. The sample may be any suitable sample. The invention is typically carried out on a sample that is known to contain or suspected of containing the peptide, polypeptide or protein.

The sample typically comprises a body fluid of the organism. The sample may be urine, lymph, saliva, mucus, milk or amniotic fluid but is preferably blood, plasma or serum.

The sample is typically processed prior to being assayed. The sample may be measured immediately upon being taken. The sample may also be typically stored prior to assay, preferably below −70° C. The method may include the purification of the peptide, polypeptide or protein of interest from the sample (e.g. by the use of specific antibodies) and its concentration/enrichment to measurable amounts, typically no less than 10-100 nM. Further, the peptide, polypeptide or protein of interest may be tagged by one of the methods described in the art. Typically the N-terminal and C-terminal groups are suitable for such tagging since they have a differential chemical reactivity. Alternatively, antibody mediated modification at specific residues is possible.

Other Applications

The method of the invention may used for other applications. For instance, it may be used to analyze physiological conditions or changes in a cell, such as the analysis of PTM changes during cell cycle, on aged cells, or during signal-transduction. The method of the invention may also be used for testing pharmaceuticals (such as for monitoring their efficacy). It may also be used for the indirect testing of drug abuse, poisons, pollutants, etc.

The method of the invention may also be used for quality control of biotherapeutics, such as to confirm that the biotherapeutic contains the correct PTM(s) or to distinguish a chemically modified biotherapeutic from naturally occurring counterparts.

The following Example illustrates the invention.

Example

We demonstrate this possibility by examining different phosphorylated forms of a protein kinase substrate. The model protein, a thioredoxin variant with the protein kinase phosphorylation sites inserted in the sequence, was tagged on a C-terminal cysteine with oligo(dC)$_{30}$. In an applied potential, the DNA leader sequence threads into the αHL pore and exerts a force on the folded protein, which causes unfolding of a C-terminal domain. The remainder of the protein then unfolds spontaneously and diffuses through the pore[37] (FIG. 1a). We have used a set of mutant thioredoxins with phosphorylation sites for the catalytic subunit of protein kinase A (PKA) at several locations near the C terminus, we phosphorylated them with PKA and tagged both the phosphorylated and non-phosphorylated forms with oligo (dC)$_{30}$. By the examination of changes in the ionic current when the C terminus moves into the pore, we have identified mono- and di-phosphorylated states of the protein and resolved the location of such sites.

Materials and Methods

αHL Nanopores

Wild-type (WT) αHL monomers were expressed in an *E. coli* in vitro transcription/translation (IVTT) system and oligomerized to form heptameric pores on rabbit red blood cell membranes. The heptameric pores were purified by sodium dodecyl sulphate (SDS) polyacrylamide gel electrophoresis[41].

Thioredoxin Mutants

The thioredoxin (Trx) V5-C109 gene was cloned into the pET 30a (+) plasmid (TopGene). The Trx mutants were produced by site-directed mutagenesis (QuickChange® II XL, Stratagene), and verified by DNA sequencing. Protein expression was performed using *E. coli* BL21(DE3) cells (Novagen) after induction with IPTG in the exponential growing phase. The proteins were purified by size-exclusion chromatography (Superdex 75 10/300 GL, Tricorn, GE Healthcare) using TE buffer (10 mM Tris.HCl, 1 mM EDTA, pH 8.3) with 1 mM DTT followed by ion-exchange chromatography (HiTrap Q FF, GE Healthcare) eluted with a gradient of 0-1 M KCl in TE buffer with 1 mM DTT, pH 8.3. Protein masses were confirmed by electrospray ionization liquid chromatography-mass spectrometry (ESI LC-MS)[37].

Catalytic Subunit of Protein Kinase A

Hexahistidine-tagged catalytic subunit of protein kinase A (PKA) was purified for site-specific serine phosphorylation of Trx mutants. The pET15b PKA Cat plasmid[42] was transformed into Rosetta (DE3)pLysS cells (Novagen). The cells were grown at 37° C. in Luria Broth containing ampicillin antibiotic (50 μg/mL) to OD$_{600}$=0.6 to 0.8. The cell culture was induced by IPTG, at a final concentration of 0.5 mM, and incubated at 18° C. for 24 h. Cells were harvested by centrifugation and lysed with BugBuster® Master Mix (Novagen) before loading into a gravity-flow Ni-NTA Superflow affinity column (Qiagen). After washing with phosphate buffer (10 mM phosphate, 150 mM NaCl, pH 7.2) the hexahistidine-tagged catalytic subunit was eluted with 500 mM imidazole in phosphate buffer. The mass of the protein was confirmed by ESI LC-MS.

Phosphorylation of Thioredoxin Mutants

Trx mutants were phosphorylated on the serine residue of the RRXS recognition sequence by using the catalytic subunit of PKA. The Trx mutants (~0.5-1 mg/mL) in 20 mM Tris.HCl buffer, containing 20 mM MgOAc, pH 7.4, were incubated with 2 mM DTT, 0.2 mM adenosine 5'-triphosphate (ATP, disodium salt hydrate, Sigma-Aldrich), and ~0.06 mg/mL PKA. The phosphorylation kinetics were followed by ESI LC-MS and isoelectric focusing (IEF) gel electrophoresis. Phosphorylation on TrxS112$^{-P}$ was complete within 2 h. For TrxS107$^{-P}$ and TrxS95$^{-P}$, additional ATP and PKA were added to increase the yield of phosphorylation and the incubation time was extended. The phosphorylated proteins were purified by size-exclusion chromatography in TE buffer (10 mM Tris.HCl, 1 mM EDTA, pH 8.3) containing 1 mM DTT (Superdex 75 10/300 GL, Tricorn, GE Healthcare).

Oligonucleotide-Thioredoxin Conjugates

Oligonucleotide-Trx conjugates were obtained as previously described[37]. Briefly, the Trx mutants and 5'-thiol (hexamethylene linker) modified oligo(dC)$_{30}$ (Integrated DNA Technologies) were separately reduced for 24 h in DTT (1 mM). DTT was removed by buffer exchange (10 mM Tris.HCl, pH 8.0) by using PD-10 Desalting Columns (GE Healthcare) and the 5'-thiol oligo(dC)$_{30}$ was activated with 2,2'-dipyridyl disulfide (10 mM in acetonitrile), purified with a PD-10 Desalting Column (GE Healthcare) and then reacted with the reduced Trx mutants for 16 h at room temperature (after buffer exchange of the proteins into 100 mM Tris.HCl, pH 10.0). The conjugates were purified by ion-exchange chromatography (HiTrap Q FF, GE Healthcare) by using a gradient of 0-1 M KCl TE buffer (10 mM Tris.HCl, 1 mM EDTA, pH 8.3). Concentrations were determined from the absorbance at 260 nm by using the calculated molar extinction coefficient of the oligo(dC)$_{30}$.

Single Channel Recordings and Data Analysis

Electrical recordings were performed with planar lipid bilayers at 21.0±2.0° C. A bilayer of 1,2-diphytanoyl-sn-glycero-3-phosphatidylcholine (Avanti Polar Lipids) was formed across an aperture of 100 μm diameter in a Teflon film (Goodfellow) separating the cis and trans compartments of the recording apparatus (1 mL each). Both compartments were filled with 10 mM HEPES, 2 M KCl, pH 7.4. Gel-purified αHL heptamers (~0.2, ~1 ng/μL) were added to the grounded cis compartment. Trx mutants were added to the cis compartment to give a final concentration of 0.1-0.2 μM. After the insertion of a single pore, the cis compartment was manually perfused with fresh buffer to prevent further insertions. Ionic currents produced by an applied potential were measured by using Ag/AgCl electrodes connected to a patch-clamp amplifier (Axopatch 200B, Axon Instruments). Signals were low-pass-filtered at 5 kHz and sampled at 25 kHz with a Digidata 1440A digitizer (Axon Instruments). Data analysis was performed with pClamp software (Molecular Devices). Events were collected by threshold searches, excluding very short events (<10 ms) and long blockades (>10 s). Residual current values ($I_{RES\ \%}$) and noise levels ($I_n$) of level 3 were determined by fitting all-points histograms (0.2 pA bin) to Gaussian curves ($I_{RES\ \%}=I_B/I_O\times100$[41]; $I_n$=standard deviation of the fit). Approximately 100 individual events for each construct were used for the 2D $I_{RES\ \%}$ versus L plots. Dwell times for levels 1, 2, and 3 were plotted as unbinned cumulative histograms and fitted to single exponentials (Igor Pro 6.12A, WaveMetrics) to obtain mean dwell times. Error bars for each construct represent the standard deviation for 3 independent experiments.

Results

Detection of Phosphorylation at a Single-Site

In previous work, we used the thioredoxin (Trx) mutant V5 (A22P, I23V, C32S, C35S, P68A) to examine co-translocational protein unfolding. This mutant lacks the catalytic disulfide and contains three stabilizing mutations (A22P, I23V, P68A). With a cysteine residue at the C terminus (Cys-109), Trx V5 could be coupled with a DNA oligonucleotide for translocation experiments[37]. For the present work, we made a mutant derived from Trx V5 with a PKA phosphorylation site (RRAS) at the C terminus (TrxS112$^{-P}$; SEQ ID NO: 12), where the underlined target serine is Ser-112 (FIG. 1b,c). We coupled the C-terminal Cys-113 of TrxS112$^{-P}$ to oligo(dC)$_{30}$ through a disulfide bond. The conjugate, TrxS112$^{-P}$-oligo(dC)$_{30}$, was translocated into the αHL pore under an applied potential of +140 mV and produced the characteristic ionic current signature (FIG. 1a) (FIG. 4) described previously[37]. In brief (FIG. 1a), the oligonucleotide leader threads into the pore (step 1 ⊠ 2), the force on the DNA unfolds a C terminal region of the protein (step 2 ⊠ 3), the remainder of the protein unfolds spontaneously (step 3 ⊠ 4), diffuses through the pore (level 4), and finally exits into the trans compartment (step 4 ⊠ 1). Step 2 ⊠ 3 (i.e. the dwell-time at level 2) is voltage-dependent, while steps 3 ⊠ 4 and 4 ⊠ 1 are voltage-independent[37].

We phosphorylated TrxS112$^{-P}$ at Ser-112 to give TrxS112$^{+P}$ by overnight incubation with ATP and the catalytic subunit of protein kinase A (PKA). Complete phosphorylation was achieved as determined by ESI LC-MS (FIG. 5). Oligo(dC)$_{30}$ was then attached at the C terminus. TrxS112$^{+P}$-oligo(dC)$_{30}$ underwent cotranslocational unfolding by the same 4-step pathway as TrxS112$^{-P}$-oligo(dC)$_{30}$ and exhibited similar translocation kinetics (FIG. 6). However, after phosphorylation, level 3 showed differences in mean residual current ($I_{RES}$) and noise ($I_n$) (FIG. 1d,e). An individual L value was the standard deviation of a Gaussian fit to an all-points histogram of the ionic current in level 3. In a typical experiment, TrxS112$^{-P}$-oligo(dC)$_{30}$ gave $I_{RES\ \%}$=18 7±0.2% of the open pore current, and $I_n$=6.0±0.1 pA (n=100, where n is the number of translocation events). With the same pore, TrxS112$^{+P}$-oligo(dC)$_{30}$ gave $I_{RES\ \%}$=20.9±0.2%, and $I_n$=5.4±0.2 pA (n=100) (FIG. 1f). We examined the voltage dependences of the ionic currents and found the largest differences in both $I_{RES\ \%}$ and L between TrxS112$^{-P}$ and TrxS112$^{+P}$ at +140 mV (FIG. 7).

Distinguishing Monophosphorylation at Three Different Sites

To explore the ability of the αHL pore to distinguish phosphorylation at different locations, we made two additional mutants based on Trx V5: TrxS107$^{-P}$ (SEQ ID NO: 13), with a phosphorylation site (RRNS) at position Ser-107 in the C-terminal α-helix of thioredoxin (FIG. 1b,g) and TrxS95$^{-P}$ (SEQ ID NO: 14), with a site (RRLS) at position Ser-95, in a loop that immediately precedes the C-terminal α-helix (FIG. 1b,k).

After coupling to oligo(dC)$_{30}$, all three non-phosphorylated proteins (TrxS95$^{-P}$, TrxS107$^{-P}$, and TrxS112$^{-P}$) gave the characteristic 4-step signal (FIG. 8). Nevertheless, the values of $I_{RES\ \%}$ and L in level 3 differed (FIG. 1d,h,l), which we attribute to the exquisite ability of nanopores to distinguish between molecules located in the lumen of the pore[39-41].

We examined each non-phosphorylated and phosphorylated protein pair with the same αHL pore in order to avoid minor differences originating from pore-to-pore variation (Table 4 below).

TABLE 4

Pore to pore variation. Residual current ($I_{RES\ \%}$) and noise
($I_n$) for all the constructs used in this work at +140
mV. Each construct was studied by using 3 different pores in 3
independent experiments (analyzing at least 50 events). Note that
constructs TrxS107/S112-oligo(dC)$_{30}$, TrxA107/S112-oligo(dC)$_{30}$, and
TrxS107/A112-oligo(dC)$_{30}$ contain two sub-levels in
level 3 unless S107 is phosphorylated.

| Construct | $I_{RES}$ Average (%) | $I_{RES}$ S.D. (%) | $I_n$ (pA) | $I_n$ S.D. (pA) |
|---|---|---|---|---|
| TrxS112$^{-P}$-oligo(dC)$_{30}$ | 18.8 | 0.1 | 5.6 | 0.4 |
| TrxS112$^{+P}$-oligo(dC)$_{30}$ | 20.9 | 0.1 | 5.1 | 0.3 |
| TrxS107$^{-P}$-oligo(dC)$_{30}$ | 16.4 | 0.4 | 6.1 | 0.3 |
| TrxS107$^{+P}$-oligo(dC)$_{30}$ | 18.4 | 1.0 | 5.8 | 0.3 |
| TrxS95$^{-P}$-oligo(dC)$_{30}$ | 22.4 | 0.4 | 4.9 | 0.1 |
| TrxS95$^{+P}$-oligo(dC)$_{30}$ | 21.5 | 0.3 | 3.8 | 0.1 |
| TrxS107$^{-P}$/S112$^{-P}$-oligo(dC)$_{30}$ | 12.8 | 0.2 | 7.0 | 0.8 |
|  | 23.2 | 1.1 | 8.8 | 1.5 |
| TrxS107$^{+P}$/S112$^{+P}$-oligo(dC)$_{30}$ | 15.2 | 0.2 | 6.2 | 0.4 |
| TrxA107/S112$^{-P}$-oligo(dC)$_{30}$ | 11.9 | 0.5 | 7.7 | 0.6 |
|  | 22.2 | 1.9 | 13.6 | 0.4 |
| TrxA107/S112$^{+P}$-oligo(dC)$_{30}$ | 13.1 | 1.0 | 6.8 | 0.7 |
|  | 20.3 | 1.0 | 5.1 | 0.6 |
| TrxS107$^{-P}$/A112-oligo(dC)$_{30}$ | 12.8 | 0.4 | 8.4 | 0.8 |
|  | 23.0 | 0.7 | 8.0 | 0.6 |
| TrxS107$^{+P}$/A112-oligo(dC)$_{30}$ | 14.8 | 0.6 | 5.6 | 0.5 |

In a typical experiment, TrxS107$^{-P}$-oligo(dC)$_{30}$, with the phosphorylation site in the C-terminal α-helix, 1 gave $I_{RES\ \%}$=16.4±0.2% and $I_n$=6.4±0.1 pA (n=99, 5 kHz filter) for level 3 at +140 mV. We phosphorylated TrxS107$^{-P}$ with PKA and ATP, and obtained almost complete phosphorylation after 48 h (during which additional PKA and ATP were added) as estimated by ESI LC-MS. After the attachment of oligo(dC)$_{30}$, a 4-step signal was obtained (FIG. 1i) with $I_{RES\ \%}$=17.9±0.2% and $I_n$=5.5±0.2 pA (n=100, 5 kHz filter) for level 3 at +140 mV. TrxS107$^{-P}$-oligo(dC)$_{30}$ and TrxS107$^{+P}$-oligo(dC)$_{30}$ could therefore readily be distinguished as two separate populations in 2D $I_{RES\ \%}$ versus $I_n$ scatter plots displaying multiple translocation events (FIG. 1j).

Similarly, before phosphorylation, in a typical measurement, TrxS95$^{-P}$-oligo(dC)$_{30}$, with the phosphorylation site in the loop, displayed a level 3 with $I_{RES\ \%}$=22.5±0.1% and $I_n$=4.9±0.1 pA (n=100, 5 kHz filter) at +140 mV. After treatment with PKA and ATP for 72 h (with three renewals of the reagents), partial phosphorylation was obtained as judged by ESI LC-MS. Upon oligo(dC)$_{30}$ attachment and examination with the αHL pore, the phosphorylated and non-phosphorylated forms could be distinguished. TrxS95$^{+P}$-oligo(dC)$_{30}$ gave a level 3 with $I_{RES\ \%}$=21.6±0.3% and $I_n$=3.8±0.1 pA (n=150, 5 kHz filter) (FIG. 1l,m,n).

Detection of Phosphorylation at Two Sites

We next made a thioredoxin construct, TrxS107$^{-P}$/S112$^{-P}$ (SEQ ID NO: 15), with two phosphorylation sites, one in the C-terminal α-helix (RRLS, Ser-107) and one in the C-terminal extension (RRAS, Ser-112) separated by an alanine residue (FIG. 1b). Two control constructs were made containing single phosphorylation sites, in one case by mutating the Ser-107 of TrxS107$^{-P}$/S112$^{-13}$ to Ala (TrxA107/S112$^{-13}$; SEQ ID NO: 16) and in the second case by mutating the Ser-112 to Ala (TrxS107$^{-P}$/A112; SEQ ID NO: 17). All three constructs carried a C-terminal cysteine (Cys-113) for oligo(dC)$_{30}$ attachment.

Again, these proteins showed the characteristic 4-step signal upon translocation through the αHL pore (FIG. 2 a,c,e). In all three cases, level 3 of the non-phosphorylated constructs comprised two rapidly interconverting sub-states. The sub-state with the lowest conductance was used for comparison with the phosphorylated proteins, because the phosphorylated proteins show only the lower state, as judged by $I_{RES\ \%}$ values. At +140 mV, the non-phosphorylated proteins gave, in a typical measurement: TrxS107$^{-P}$/S112$^{-P}$-oligo(dC)$_{30}$ $I_{RES\ \%}$=13.0±0.2%, $I_n$=7.9±0.4 pA (n=100); TrxA107/S112$^{-P}$-oligo(dC)$_{30}$ $I_{RES\ \%}$=12.3±0.2%, $I_n$=8.4±0.6 pA (n=100); TrxS107$^{-P}$/A112-oligo(dC)$_{30}$ $I_{RES\ \%}$=13.2±0.2%, $I_n$=8.7±0.6 pA (n=100) (FIGS. 9, 10). The detectable differences in $I_{RES\ \%}$ and L illustrate the ability of protein nanopores to distinguish subtle variations in polypeptide structure (i.e. Ser ⊗ Ala).

We next phosphorylated each construct with PKA. Complete phosphorylation of TrxA107/S112$^{-P}$ took less than 2 h, while TrxS107$^{-P}$/A112 and TrxS107$^{-P}$/S112$^{-P}$ required 44 h with replenishment of the reagents to attain almost complete phosphorylation (FIG. 11). The phosphorylated constructs again showed distinctive $I_{RES\ \%}$ and L values in level 3 (FIG. 2b,d,f): TrxS107$^{+P}$/S112$^{+P}$-oligo(dC)$_{30}$ $I_{RES\ \%}$=15.2±0.2%, $I_n$=5.7±0.1 pA (n=98); TrxS107$^{-P}$/S112$^{-P}$-oligo(dC)$_{30}$ $I_{RES\ \%}$ 12.6±0.1%, $I_n$=6.2±0.2 pA (n=100); TrxA107/S112$^{+P}$-oligo(dC)$_{30}$ $I_{RES\ \%}$=13.8±0.2%, $I_n$=6.8±0.2 pA (n=65); TrxS107$^{+P}$/A112-oligo(dC)$_{30}$, $I_{RES\ \%}$=14.6±0.2%, In =5.1±0.2 pA) (n=79) (FIG. 2g, FIG. 11).

Incomplete Phosphorylation at Two Sites

Based on the ability to distinguish monophosphorylation at Ser-107 and Ser-112, and phosphorylation of both sites, we examined the incomplete phosphorylation of TrxS107$^{-P}$/S112$^{-P}$. We monitored the time-course of phosphorylation by isoelectric focusing (IEF) (FIG. 3a), which showed that after 2 h two populations of phosphorylated protein are present, one doubly phosphorylated and the other phosphorylated at just one site. IEF cannot distinguish phosphorylation at Ser-107 from phosphorylation at Ser-112. However, ESI LC-MS showed that TrxA107/S112$^{-P}$ is almost completely phosphorylated after 2 h, while TrxS107$^{-P}$/A112 is not fully phosphorylated even after 48 h with the further addition of PKA and ATP. Therefore, the two phosphorylated species derived from TrxS107$^{-P}$/S112$^{-P}$ after 2 h are likely to be that with only Ser-112 phosphorylated and that with both sites phosphorylated.

After 2 h of phosphorylation, the TrxS107$^{-P}$/S112$^{-P}$ sample was tagged with oligo(dC)$_{30}$ and subjected to nanopore analysis, which showed that the mixture contained two populations, one with $I_{RES\ \%}$=15.4±0.1%, $I_n$=5.7±0.1 pA and the other with $I_{RES\ \%}$=14.3±0.1%, $I_n$=6.7±0.1 pA (FIG. 3b). Based on the nanopore calibration (FIG. 13), these species correspond to the doubly phosphorylated species TrxS107$^{+P}$/S112$^{+P}$ ($I_{RES\ \%}$=15.4±0.2%, $I_n$=5.7±0.1 pA) and the protein phosphorylated on Ser-112, represented by TrxA107/S112$^{+P}$-oligo(dC)$_{30}$ ($I_{RES\ \%}$=14.0±0.3%, $I_n$=6.9±0.3 pA). By contrast, TrxS107$^{+P}$/A112-oligo(dC)$_{30}$, gave $I_{RES\ \%}$=14.9±0.1%, $I_n$=5.2±0.1 pA and the TrxS107$^{-P}$/S112$^{-P}$-oligo(dC)$_{30}$ gave $I_{RES\ \%}$=13.0±0.1%, $I_n$=6.5±0.1 pA). From the IEF band intensities, the sample was estimated to contain 39% doubly phosphorylated and 61% singly phosphorylated thioredoxin. In accord with this, based on 202 single-molecule events, we found 67 molecules (33%) to be doubly phosphorylated and 123 molecules (61%) to be singly phosphorylated at Ser112 with just one (0.5%) singly phosphorylated at Ser107.

DISCUSSION

Based on our earlier finding that a model protein equipped with a DNA leader sequence can be translocated through the αHL pore and simultaneously unfolded, providing a characteristic ionic current signature[37], we now find that side-chain phosphorylation, an important PTM, can be detected at the single-molecule level through alterations in the current signature. Remarkably, phosphorylation at different locations in the protein result in different signatures, which allows rapid discrimination between sites of modification. We also show that the phosphorylation states of two adjacent sites (separated by one residue) can be distinguished and quantified: namely, the unphosphorylated state, the two monophosphorylated states, and the doubly phosphorylated state. Proteins monophosphorylated on one of two adjacent sites are especially difficult to distinguish by MS, and we suggest that the occupancy and connectivity of phosphorylation sites within a single polypeptide chain is a problem ideally suited for the nanopore approach.

REFERENCES

1. Khoury, G. A., Baliban, R. C. & Floudas, C. A. Proteome-wide post-translational modification statistics: frequency analysis and curation of the swiss-prot database. *Sci. Rep.* 1 (2011)
2. Huttlin, E. L. et al. A tissue-specific atlas of mouse protein phosphorylation and expression. *Cell* 143 1174-89 (2010)
3. Ptacek, J. et al. Global analysis of protein phosphorylation in yeast. *Nature* 438 679-84 (2005)
4. Kruse, J. P. & Gu, W. SnapShot: p53 posttranslational modifications. *Cell* 133 930-30 (2008)
5. MacLaine, J. M. & Hupp, T. R. How phosphorylation controls p53. *Cell Cycle* 10 916-21 (2011)
6. Brooks, C. L. & Gu, W. New insights into p53 activation. *Cell Res.* 20 614-21 (2010)
7. Unlu, M., Morgan, M. E. & Minden, J. S. Difference gel electrophoresis: a single gel method for detecting changes in protein extracts. *Electrophoresis* 18 2071-7 (1997)
8. Gorg, A., Weiss, W. & Dunn, M. J. Current two-dimensional electrophoresis technology for proteomics. *Proteomics* 4 3665-85 (2004)
9. Choudhary, C. & Mann, M. Decoding signalling networks by mass spectrometry-based proteomics. *Nat. Rev. Mol. Cell. Biol.* 11 427-39 (2010)
10. Domon, B. & Aebersold, R. Mass spectrometry and protein analysis. *Science* 312 212-7 (2006)
11. Mertins, P. et al. Integrated proteomic analysis of post-translational modifications by serial enrichment. *Nat. Methods* 10 634-7 (2013)
12. Bayley, H. & Cremer, P. S. Stochastic sensors inspired by biology. *Nature* 413 226-30 (2001)
13. Howorka, S. & Siwy, Z. Nanopore analytics: sensing of single molecules. *Chem. Soc. Rev.* 38 2360-84 (2009)
14. Braha, O. et al. Simultaneous stochastic sensing of divalent metal ions. *Nat. Biotechnol.* 18 1005-7 (2000)
15. Kang, X. F., Cheley, S., Guan, X. & Bayley, H. Stochastic detection of enantiomers. *J. Am. Chem. Soc.* 128 10684-5 (2006)
16. Wu, H. C. & Bayley, H. Single-molecule detection of nitrogen mustards by covalent reaction within a protein nanopore. *J. Am. Chem. Soc.* 130 6813-9 (2008)
17. Bayley, H. Sequencing single molecules of DNA. *Curr. Opin. Chem. Biol.* 10 628-37 (2006)
18. Branton, D. et al. The potential and challenges of nanopore sequencing. *Nat. Biotechnol.* 26 1146-53 (2008)
19. Cockroft, S. L., Chu, J., Amorin, M. & Ghadiri, M. R. A single-molecule nanopore device detects DNA polymerase activity with single-nucleotide resolution. *J. Am. Chem. Soc.* 130 818-20 (2008)
20. Olasagasti, F. et al. Replication of individual DNA molecules under electronic control using a protein nanopore. *Nat. Nanotechnol.* 5 798-806 (2010)
21. Chu, J., Gonzalez-Lopez, M., Cockroft, S. L., Amorin, M. & Ghadiri, M. R. Real-time monitoring of DNA polymerase function and stepwise single-nucleotide DNA strand translocation through a protein nanopore. *Angew. Chem. Int. Ed. Engl.* 49 10106-9 (2010)
22. Lieberman, K. R. et al. Processive replication of single DNA molecules in a nanopore catalyzed by phi29 DNA polymerase. *J. Am. Chem. Soc.* 132 17961-72 (2010)
23. Hayden, E. C. Sequence set to alter clinical landscape. *Nature* 482 288 (2012)
24. Pennisi, E. Genome sequencing. Search for pore-fection. *Science* 336 534-7 (2012)
25. Bayley, H. Are we there yet?: Comment on "Nanopores: A journey towards DNA sequencing" by Meni Wanunu. *Phys. Life Rev.* 9 161-3 (2012)
26. Cherf, G. M. et al. Automated forward and reverse ratcheting of DNA in a nanopore at 5-A precision. *Nat. Biotechnol.* 30 344-8 (2012)
27. Manrao E. A. et al. Reading DNA at single-nucleotide resolution with a mutant MspA nanopore and phi29 DNA polymerase. *Nat. Biotechnol.* 30 349-53 (2012)
28. Stoddart, D., Heron, A. J., Mikhailova, E., Maglia, G. & Bayley, H. Single-nucleotide discrimination in immobilized DNA oligonucleotides with a biological nanopore. *Proc. Natl. Acad. Sci. U.S.A.* 106 7702-7 (2009)
29. Purnell, R. F. & Schmidt, J. J. Discrimination of single base substitutions in a DNA strand immobilized in a biological nanopore. *ACS Nano* 3 2533-8 (2009)
30. Derrington, I. M. et al. Nanopore DNA sequencing with MspA. *Proc. Natl. Acad. Sci. U.S.A.* 107 16060-5 (2010)
31. Manrao, E. A., Derrington, I. M., Pavlenok, M., Niederweis, M. & Gundlach, J. H. Nucleotide discrimination with DNA immobilized in the MspA nanopore. *PLoS One* 6 (2011)
32. Movileanu, L., Howorka, S., Braha, O. & Bayley, H. Detecting protein analytes that modulate transmembrane movement of a polymer chain within a single protein pore. *Nat. Biotechnol.* 18 1091-5 (2000)
33. Xie, H. Braha, O., Gu, L. Q., Cheley, S. & Bayley, H. Single-molecule observation of the catalytic subunit of cAMP-dependent protein kinase binding to an inhibitor peptide. *Chem. Biol.* 12 109-20 (2005)
34. Howorka, S., Nam, J., Bayley, H. & Kahne, D. Stochastic detection of monovalent and bivalent protein-ligand interactions. *Angew. Chem. Int. Ed. Engl.* 43 842-6 (2004)
35. Rotem, D., Jayasinghe, L., Salichou, M., Bayley, H. Protein detection by nanopores equipped with aptamers. *J. Am. Chem. Soc.* 134 2781-7 (2012)
36. Merstorf, C. et al. Wild type, mutant protein unfolding and phase transition detected by single-nanopore recording. *ACS Chem. Biol.* 7 652-8 (2012)
37. Rodriguez-Larrea, D. & Bayley, H. Multistep protein unfolding during nanopore translocation. *Nat. Nanotechnol.* 8 288-95 (2013)
38. Nivala, J., Marks, D. B. & Akeson, M. Unfoldase-mediated protein translocation through an α-hemolysin nanopore. *Nat. Biotechnol.* 31 247-50 (2013)
39. Kang, X. F., Cheley, S., Guan, X. & Bayley, H. Stochastic detection of enantiomers. *J. Am. Chem. Soc.* 128 10684-5 (2006)
40. Shin, S. H., Steffensen, M. B., Claridge, T. D., Bayley, H. Formation of a chiral center and pyrimidal inversion at the single-molecule level. *Angew. Chem. Int. Ed. Engl.* 46 7412-6 (2007)

41. Wallace, E. V. et al. Identification of epigenetic DNA modifications with a protein nanopore. *Chem. Commun.* 46 8195-7 (2010)
42. Bayley, H. et al. *Droplet interface bilayers. Mol. Biosyst.* 4 1191-208 (2008)
43. Maglia, G., Heron, A. J., Stoddart, D., Japrung, D. & Bayley, H. Analysis of single nucleic acid molecules with protein nanopores. *Methods Enzymol.* 475 591-623 (2010)
44. Narayana, N., Cox, S., Shaltiel, S., Taylor, S. S. & Xuong, N. Crystal structure of a polyhistidine-tagged recombinant catalytic subunit of cAMP-dependent protein kinase complexed with the peptide inhibitor PKI(5-24) and adenosine. Biochemistry 36 4438-48 (1997)
45. Cohen, *European Journal of Biochemistry*, 268, Issue 19, pages 5001-5010, October 2001

---

The invention claimed is:

1. A method for determining the number or position(s) of two or more post-translational modifications (PTMs) in a peptide, polypeptide or protein, the method comprising:
   (a) contacting the peptide, polypeptide or protein with a transmembrane pore such that the peptide, polypeptide or protein moves through the pore; and
   (b) taking one or more current measurements as the peptide, polypeptide or protein moves with respect to the pore and thereby determining the number or position(s) of two or more PTMs in the peptide, polypeptide or protein;
   wherein the peptide, polypeptide or protein is covalently attached to a single-stranded oligonucleotide.

2. A method according to claim 1, wherein the method is for determining the number or positions of two or more PTMs in a peptide, polypeptide or protein which are separated by 1, 2, 3 or 4 amino acids.

3. A method according to claim 1, wherein the two or more PTMs are selected from the group consisting of modification with a hydrophobic group, modification with a cofactor, addition of a chemical group, glycation, biotinylation and pegylation.

4. A method according to claim 3, wherein:
   (a) the modification with a hydrophobic group is selected from the group consisting of myristoylation, palmitoylation, isoprenylation, prenylation, farnesylation, geranylgeranylation and glypiation;
   (b) the modification with a cofactor is selected from the group consisting of lipoylation, flavination, attachment of heme C, phosphopantetheinylation and retinylidene Schiff base formation; and
   (c) the addition of a chemical group is selected from the group consisting of acylation, acetylation, formylation, alkylation, amidation, butyrylation, gamma-carboxylation, glycosylation, polysialylation, malonylation, hydroxylation, iodination, bromination; citrulination; nucleotide addition, ADP ribosylation, oxidation, phosphorylation, adenylylation, propionylation, pyroglutamate formation, S-glutathionylation, Sumoylation; S-nitrosylation, succinylation, selenoylation and ubiquitinilation.

5. A method according to claim 1, wherein the two or more PTMs are two or more phosphorylations.

6. A method according to claim 1, wherein the transmembrane pore is present in a membrane, and wherein the peptide, polypeptide or protein is coupled to the membrane.

7. A method according to claim 6, wherein the peptide, polypeptide or protein is coupled to the membrane using cholesterol.

8. A method according to claim 6, wherein the membrane is an amphiphilic layer and the peptide, polypeptide or protein is coupled to the membrane via a hydrophobic anchor present in the membrane.

9. A method according to claim 1, wherein the pore is a transmembrane protein pore, a solid state pore or a hybrid membrane-solid state pore.

10. A method according to claim 9, wherein the transmembrane protein pore is derived from a hemolysin, leukocidin, *Mycobacterium smegmatis* porin A (MspA), outer membrane phospholipase A, *Neisseria* autotransporter lipoprotein (NalP), an outer membrane protein or Wza.

11. A method according to claim 10, wherein the transmembrane protein is (a) formed of seven identical subunits as shown in SEQ ID NO: 2 or (b) a variant thereof in which one or more of the seven subunits has at least 50% homology to SEQ ID NO: 2 based on amino acid identity over the entire sequence and which retains pore activity.

12. A method according to claim 10, wherein the transmembrane protein is (a) γ-hemolysin formed of four identical subunits as shown in SEQ ID NO: 4 and four identical subunits as shown in SEQ ID NO: 6 or (b) a variant thereof in which one or more of the subunits has at least 50% homology to SEQ ID NO: 4 based on amino acid identity over the entire sequence and/or one or more of the subunits has at least 50% homology to SEQ ID NO: 6 based on amino acid identity over the entire sequence and the pore retains pore activity.

13. A method according to claim 10, wherein the transmembrane protein is (a) formed of seven identical subunits as shown in SEQ ID NO: 8 or (b) a variant thereof in which one or more of the seven subunits has at least 50% homology to SEQ ID NO: 8 based on amino acid identity over the entire sequence and which retains pore activity.

14. A method according to claim 1, wherein the peptide, polypeptide or protein is covalently attached by its amino (N-) or carboxy (C-) terminus to the oligonucleotide.

15. A method according to claim 1, wherein the peptide, polypeptide or protein is covalently attached to the oligonucleotide via a linker.

16. A method of determining whether or not an organism has a disease, disorder or phenotype associated with two or more abnormal PTMs of a peptide, polypeptide or protein, the method comprising:
   (a) carrying out a method according to claim 1 on a sample from the organism comprising the peptide, polypeptide or protein; and
   (b) determining whether or not the two or more PTMs of the peptide, polypeptide or protein are present and thereby determining whether or not the organism has the disease, disorder or phenotype.

17. A method according to claim 16, wherein the method is for determining whether or not the organism has a disease, disorder or phenotype associated with abnormal phosphorylation of a peptide, polypeptide or protein.

18. A method according to claim 16, wherein the disease or disorder is cancer, chronic inflammatory disease, myotonic muscular dystrophy, X-Linked agammaglobulinaemia, Bruton tyrosine kinase, hirschsprungis disease, autosomal recessive SCID, X-Linked SCID, chraniosynostosis, papillary renal cancer, chronic myelomonocytic leukaemia, chronic myelogenous leukaemia, non-Hodgkins lymphoma, Peutz-Jeghers syndrome, Coffin-Lowry syndrome, ataxia-telangiectasia, Li-Fraumeni syndrome, Williams syndrome, Leprechaunism, diabetes, Wolff-Parkinson-White syndrome, Wolcott-Rallison syndrome or X-Linked myotubular myopathy.

19. A method according to claim 16, wherein the two or more PTMs are two or more phosphorylations.

* * * * *